(12) United States Patent
Chen et al.

(10) Patent No.: US 11,680,050 B2
(45) Date of Patent: Jun. 20, 2023

(54) CRYSTALLINE FORMS OF OZANIMOD AND OZANIMOD HYDROCHLORIDE, AND PROCESSES FOR PREPARATION THEREOF

(71) Applicant: RECEPTOS LLC, New York, NY (US)

(72) Inventors: Minhua Chen, Suzhou (CN); Xiaoyu Zhang, Suzhou (CN); Yanfeng Zhang, Suzhou (CN); Chaohui Yang, Suzhou (CN); Xiaoting Zhai, Suzhou (CN); Kaiqiang Yan, Suzhou (CN)

(73) Assignee: RECEPTOS LLC, New York, NY (US)

( * ) Notice: Subject to any disclaimer, the term of this patent is extended or adjusted under 35 U.S.C. 154(b) by 473 days.

(21) Appl. No.: 16/748,303

(22) Filed: Jan. 21, 2020

(65) Prior Publication Data

US 2020/0157065 A1 May 21, 2020

Related U.S. Application Data

(63) Continuation of application No. 16/310,328, filed as application No. PCT/CN2017/088314 on Jun. 14, 2017, now Pat. No. 11,111,223.

(30) Foreign Application Priority Data

Jun. 14, 2016 (CN) .......................... 201610416179.8
Jun. 29, 2016 (CN) .......................... 201610493910.7

(51) Int. Cl.
*C07D 271/06* (2006.01)

(52) U.S. Cl.
CPC ........ *C07D 271/06* (2013.01); *C07B 2200/13* (2013.01)

(58) Field of Classification Search
CPC .................................................. C07D 271/06
See application file for complete search history.

(56) References Cited

U.S. PATENT DOCUMENTS

| | | | | |
|---|---|---|---|---|
| 2011/0172202 A1 * | 7/2011 | Martinborough | ..... | C07C 311/13 514/210.18 |
| 2019/0248755 A1 | 8/2019 | Chen et al. | | |
| 2019/0337908 A1 | 11/2019 | Chen et al. | | |
| 2020/0031784 A1 * | 1/2020 | Sheng | .................. | C07D 271/06 |

FOREIGN PATENT DOCUMENTS

| | | | |
|---|---|---|---|
| CN | 102118972 A | 7/2011 | |
| CN | 102762100 A | 10/2012 | |
| CN | 107840830 A | 3/2018 | |
| WO | 2009/151529 A1 | 12/2009 | |
| WO | 2011/060392 A1 | 5/2011 | |
| WO | 2015/066515 A1 | 5/2015 | |
| WO | 2016/164180 A1 | 10/2016 | |
| WO | 2017/215617 A1 | 12/2017 | |
| WO | 2018/049632 A1 | 3/2018 | |
| WO | 2018/050091 A1 | 3/2018 | |

OTHER PUBLICATIONS

International Search Report and Written Opinion for Application No. PCT/CN2017/088314, dated Aug. 30, 2017, 13 pages.
U.S. Appl. No. 16/310,328, filed Dec. 14, 2018, 2019-0337908, Published.
Byrn et al., Pharmaceutical solids: a strategic approach to regulatory considerations Pharm Res. 1995;12(7):945-954.
Caira, Crystalline Polymorphism of Organic Compounds. Topics in Current Chemistry. 1998; 198;163-208.
Huan, Journal of International Pharmaceutical Research. Aug. 31, 2016;43(4):786.
Jacob et al., Solid State Crystallinity, Amorphous State, and Its Implications in the Pharmaceutical Process. IJPSR, 2011 2(3):472-482.
Jiang et al., Research and Development of Sphingosine 1-Phosphate Modulators Progress in Pharmaceutical Sciences. Jul. 31, 2016;40(7):548-554.
Scott et al., Ozanimod (RPC1063) is a potent sphingosine-1-phosphate receptor-1 (S1P1 ) and receptor-5 (S1P5 ) agonist with autoimmune disease-modifying activity. Br J Pharmacol. 2016;173(11):1778-1792.
International Search Report and Written Opinion for Application No. PCT/CN2018/102034, dated Nov. 29, 2018, 11 pages.

* cited by examiner

*Primary Examiner* — Matthew P Coughlin
(74) *Attorney, Agent, or Firm* — McCarter & English, LLP; Wei Song

(57) ABSTRACT

The present disclosure is directed to novel crystalline forms of ozanimod and ozanimod hydrochloride, as well as preparation method thereof. Said crystalline forms of ozanimod and ozanimod hydrochloride can be used for treating autoimmune diseases, particularly used for preparing drugs for treating multiple sclerosis and ulcerative colitis. The crystalline forms of the present disclosure have one or more advantages in solubility, melting point, stability, dissolution, bioavailability and processability and provide new and better choices for the preparation of ozanimod drug product, and are very valuable for drug development.

7 Claims, 25 Drawing Sheets

CRYSTALLINE FORMS OF OZANIMOD AND OZANIMOD HYDROCHLORIDE, AND PROCESSES FOR PREPARATION THEREOF

CROSS-REFERENCE TO RELATED APPLICATIONS

This application is a continuation of U.S. patent application Ser. No. 16/310,328, filed on Dec. 14, 2018, which is National Stage Entry of International Application No. PCT/CN2017/088314, filed on Jun. 14, 2017, which, in turn, claims the benefit of foreign priority of Chinese Patent Application No.: 201610493910.7, filed on Jun. 29, 2016, and Chinese Patent Application No.: 201610416179.8, filed on Jun. 14, 2016. The entire contents of the aforementioned applications are incorporated herein by reference.

TECHNICAL FIELD

The present disclosure relates to the field of pharmaceutical chemistry, particularly relates to crystalline forms of ozanimod and ozanimod hydrochloride, and processes for preparation thereof.

BACKGROUND

Ozanimod is a novel, oral, selective modulator of sphingosine-1-phosphate 1 receptor (S1P1R) developed by Receptos for the treatment of autoimmune diseases. ozanimod is in phase III trials in the USA for the treatment of multiple sclerosis (MS) and ulcerative colitis (UC). Ozanimod has very excellent pharmacokinetics, pharmacodynamics and safety data in clinical trials, which can perfectly meet the differentiated development strategy and is expected to be the best second-generation S1P1R modulator drug. The chemical structure of the drug is shown as formula

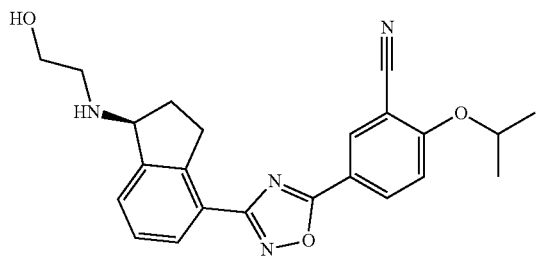

(I)

A specific pharmaceutical activity is the basic prerequisite to be fulfilled by a pharmaceutically active agent to be approved as a medicament on the market. However, there are a variety of additional requirements that a pharmaceutically active agent has to comply with. These requirements are based on various parameters which are connected with the nature of the active substance itself. Without being restricted, examples of these parameters are the chemical stability, solid-state stability and storage stability of the active substance under various environmental conditions, stability during production of the pharmaceutical composition and the stability of the active substance in the final drug products, etc.

The pharmaceutically active agent used for preparing the pharmaceutical compositions should be as pure as possible and its stability in long-term storage must be guaranteed under various environmental conditions. It is essential to prevent using pharmaceutical compositions which contain agent other than the actual active agent, for example decomposition products thereof. In such cases the content of active agent in the drug might be less than that specified. In addition it is important that the pharmaceutically active agent should be non-hygroscopic, stable both to degradation and subsequent solid form changes. If the pharmaceutically active agent is hygroscopic in the sense that it absorbs water (either slowly or over time), it is almost impossible to reliably formulate the pharmaceutically active agent into a drug as the amount of agent to be added to provide the same dosage will vary greatly depending upon the degree of hydration. Furthermore, variations in hydration or solid form can lead to changes in physicochemical properties, such as solubility or dissolution rate, which can in turn lead to inconsistent oral absorption of the patient. Preferably, therefore, a pharmaceutically active substance should be only slightly hygroscopic.

Accordingly, chemical stability, solid-state stability, "shelf life" and materials handling properties (such as ease of solubilizing the compound) of the pharmaceutically active substance are very important factors. In an ideal situation, the pharmaceutically active substance and any compositions containing it should be capable of being effectively stored over appreciable periods of time, without exhibiting a significant change in the physicochemical properties of the active substance such as its activity, moisture content, solubility, solid form, etc. Further, the pharmaceutically active substance usually needs to be processed to achieve a particle size suitable for inhalation and any crystalline form must be stable during such processing so that the properties of the final product are predictable and reliable. In short, in the production of commercially viable and pharmaceutically acceptable pharmaceutical compositions, it is desirable to provide the pharmaceutically active substance in a fully crystalline and stable form, wherever possible.

Different crystalline forms of the same solid chemical drug are significantly different in solubility and stability which can in turn affect the absorption and bioavailability of the drug products. CN102762100A or US2011172202A1 disclosed the compound of formula (I), while there is no solid form or crystalline form of ozanimod disclosed in the prior art. The prior art has neither guidance nor inspiration for finding the crystalline forms. Therefore, it is necessary to perform comprehensive polymorph screening of ozanimod to select a crystalline form which is the most suitable for drug development.

The inventors of the present disclosure have found several crystalline forms of ozanimod and a crystalline form of ozanimod hydrochloride through research process, which provides new choices for the preparation of ozanimod drug product.

SUMMARY

The present disclosure provides novel crystalline forms of ozanimod and ozanimod hydrochloride, and processes for preparation and use thereof.

One objective of the present disclosure is to provide a crystalline form of ozanimod, designated as Form CS1.

The X-ray powder diffraction pattern of Form CS1 shows characteristic peaks at 2theta values of 12.1°±0.2°, 10.4°±0.2° and 4.2°±0.2° using CuKα radiation. Furthermore, the X-ray powder diffraction pattern of Form CS1 shows one or two or three diffraction peaks at 2theta values of 7.4°±0.2°, 24.3°±0.2° and 17.7°±0.2°. Preferably, the X-ray powder diffraction pattern of Form CS1 shows three diffraction peaks at 2theta values of 7.4°±0.2°, 24.3°±0.2°, 17.7°±0.2°.

Furthermore, the X-ray powder diffraction pattern of Form CS1 shows one or two or three characteristic peaks at 2theta values of 12.8°±0.2°, 21.5°±0.2° and 18.2°±0.2°. Preferably, the X-ray powder diffraction pattern of Form CS1 shows three diffraction peaks at 2theta values of 12.8°±0.2°, 21.5°±0.2° and 18.2°±0.2°.

Furthermore, the X-ray powder diffraction pattern of Form CS1 shows characteristic peaks at 2theta values of 4.2°±0.2°, 7.4°±0.2°, 10.4°±0.2°, 12.1°±0.2°, 12.8°±0.2°, 17.7°±0.2°, 18.2°±0.2°, 21.5°±0.2° and 24.3°±0.2°.

In a preferred embodiment, the X-ray powder diffraction pattern of Form CS1 is substantially as depicted in FIG. 1.

In a preferred embodiment, the differential scanning calorimetry (DSC) curve of Form CS1 shows the first endothermic peak when heated to around 98° C. and the second endothermic peak when heated to around 134° C., which is substantially as depicted in FIG. 2.

In a preferred embodiment, the thermal gravimetric analysis (TGA) curve of Form CS1 shows about 4.3% weight loss when heated to 150° C., which is substantially as depicted in FIG. 3.

The present disclosure further provides the process for preparing Form CS1. The process comprises method 1) or method 2):

1) Suspending ozanimod hydrochloride into a solvent selected from alcohols, ketones, esters and nitriles and the suspension becomes clear after adding 1.0 to 1.5 (preferably 1.0) equivalent of sodium hydroxide solution. Then, white solid precipitates from the solution after stirring at room temperature for a period of time. Isolating the white solid by centrifugation, and then Form CS1 is obtained after drying the isolated solid. Said stirring time is at least 0.5 h, more preferably at least 1 h, further more preferably 12 h; or 2) Suspending ozanimod in an alcohol, stirring, isolating and drying the solid to obtain Form CS1 of ozanimod; wherein said stirring time is at least 0.5 hour, more preferably at least 1 h, further more preferably 12 h.

Furthermore, in method 1), said alcohol is methanol; said ketone is acetone; said ester is isopropyl acetate; said nitrile is acetonitrile. In method 2), said alcohol is methanol.

Another objective of the present disclosure is to provide a crystalline form of ozanimod, designated as Form CS2.

The X-ray powder diffraction pattern of Form CS2 shows characteristic peaks at 2theta values of 23.2°±0.2°, 18.5°±0.2° and 13.3°±0.2° using CuKα radiation.

Furthermore, the X-ray powder diffraction pattern of Form CS2 shows one or two or three diffraction peaks at 2theta values of 15.9°±0.2°, 30.0°±0.2° and 14.2°±0.2°. Preferably, the X-ray powder diffraction pattern of Form CS2 shows three diffraction peaks at 2theta values of 15.9°±0.2°, 30.0°±0.2° and 14.2°±0.2°.

Furthermore, the X-ray powder diffraction pattern of Form CS2 shows one or two or three characteristic peaks at 2theta values of 4.0°±0.2°, 26.5°±0.2° and 17.7°±0.2°. Preferably, the X-ray powder diffraction pattern of Form CS2 shows three diffraction peaks at 2theta values of 4.0°±0.2°, 26.5°±0.2° and 17.7°±0.2°.

Furthermore, the X-ray powder diffraction pattern of Form CS2 shows characteristic peaks at 2theta values of 4.0°±0.2°, 13.3°±0.2°, 14.2°±0.2°, 15.9°±0.2°, 17.7°±0.2°, 18.5°±0.2°, 23.2°±0.2°, 26.5°±0.2° and 30.0°±0.2°.

In a preferred embodiment, the X-ray powder diffraction pattern of Form CS2 is substantially as depicted in FIG. 4.

In a preferred embodiment, the differential scanning calorimetry (DSC) curve of Form CS2 shows an endothermic peak when heated to around 134° C., which is substantially as depicted in FIG. 5.

In a preferred embodiment, the thermal gravimetric analysis (TGA) curve of Form CS2 shows about 1.1% weight loss when heated to 150° C., which is substantially as depicted in FIG. 6.

The present disclosure further provides the process for preparing Form CS2. The process comprises method 1) or method 2):

1) The crystalline Form CS2 is prepared by heating Form CS1 to 100-130° C., or

2) Suspending ozanimod into a solvent selected from nitriles, ketones, esters, aromatic hydrocarbons, cyclic ethers and water, or a mixture of solvents selected from alcohols and water, ketones and water, amides and water, and then stirring, isolating and drying the solid to obtain Form CS2 of ozanimod; said stirring time is at least 0.5 hour, more preferably at least 1 h, further more preferably 12 h.

Furthermore, said heating temperature in method 1) is 110° C.

Furthermore, in method 2), said nitrile is acetonitrile; said ketone is acetone or methyl isobutyl ketone; said ester is ethyl acetate; said aromatic hydrocarbons is toluene; said cyclic ether is 2-methyltetrahydrofuran; said mixture of solvents is mixture of ethanol and water, acetone and water, or N, N-dimethylformamide and water.

Another objective of the present disclosure is to provide a crystalline form of ozanimod, designated as Form CS3.

The X-ray powder diffraction pattern of Form CS3 shows at least one characteristic peak at 2theta values of 4.4°±0.2°, 5.7°±0.2°, 7.8°±0.2°, 11.0°±0.2°, 13.0°±0.2°, 13.7°±0.2°, 17.0°±0.2°, 23.2°±0.2°, 24.1°±0.2° and 26.0°±0.2°.

Furthermore, the X-ray powder diffraction pattern of Form CS3 shows characteristic peaks at 2theta values of 4.4°±0.2°, 13.0°±0.2°, 26.0°±0.2° and 11.0°±0.2°.

Furthermore, the X-ray powder diffraction pattern of Form CS3 shows one or two or three diffraction peaks at 2theta values of 7.8°±0.2°, 23.2°±0.2° and 17.0°±0.2°. Preferably, the X-ray powder diffraction pattern of Form CS3 shows three diffraction peaks at 2theta values of 7.8°±0.2°, 23.2°±0.2° and 17.0°±0.2°.

Furthermore, the X-ray powder diffraction pattern of Form CS3 shows one or two characteristic peaks at 2theta values of 13.7°±0.2° and 24.1°±0.2°. Preferably, the X-ray powder diffraction pattern of Form CS3 shows two diffraction peaks at 2theta values of 13.7°±0.2° and 24.1°±0.2°.

Furthermore, the X-ray powder diffraction pattern of Form CS3 shows one or two characteristic peaks at 2theta values of 5.7°±0.2° and 24.1°±0.2°. Preferably, the X-ray powder diffraction pattern of Form CS3 shows two diffraction peaks at 2theta values of 5.7°±0.2° and 24.1°±0.2°.

In a preferred embodiment, the X-ray powder diffraction pattern of Form CS3 shows characteristic peaks at 2theta values of 4.4°±0.2°, 7.8°±0.2°, 11.0°±0.2°, 13.0°±0.2°, 13.7°±0.2°, 17.0°±0.2°, 23.2°±0.2°, 24.1°±0.2° and 26.0°±0.2°.

In a preferred embodiment, the X-ray powder diffraction pattern of Form CS3 is substantially as depicted in FIG. 7.

In a preferred embodiment, the differential scanning calorimetry (DSC) curve of Form CS3 shows the first endothermic peak when heated to around 112° C., shows an exothermic peak when heated to around 121° C. and shows the second endothermic peak when heated to around 133° C. which is substantially as depicted in FIG. 8.

In a preferred embodiment, the thermal gravimetric analysis (TGA) curve of Form CS3 shows about 3.1% weight loss when heated to 130° C., which is substantially as depicted in FIG. 9.

In a preferred embodiment, the X-ray powder diffraction pattern of Form CS3 shows characteristic peaks at 2theta values of 4.4°±0.2°, 5.7°±0.2°, 7.8°±0.2°, 11.0°±0.2°, 13.0°±0.2°, 17.0°±0.2°, 23.2°±0.2°, 24.1°±0.2° and 26.0°±0.2°.

In a preferred embodiment, the X-ray powder diffraction pattern of Form CS3 is substantially as depicted in FIG. 53.

Another objective of the present disclosure is to provide the process for preparing Form CS3 of ozanimod. The process comprises: adding ozanimod into a solvent selected form alcohols, nitriles, dichloromethane, esters, sulfoxides or a mixture of glycol dimethyl ether and water, filtering, evaporating the filtrate and collecting the solid to obtain Form CS3 of ozanimod.

Preferably, said alcohol is methanol; said nitrile is acetonitrile; said ester is isopropyl acetate; said sulfoxide is dimethyl sulfoxide.

Another objective of the invention is to provide a crystalline form of ozanimod, designated as Form CS5.

The X-ray powder diffraction pattern of Form CS5 shows characteristic peaks at 2theta values of 4.3°±0.2°, 6.8°±0.2° and 16.4°±0.2° using CuKα radiation.

Furthermore, the X-ray powder diffraction pattern of Form CS5 shows one or two or three diffraction peaks at 2theta values of 21.6°±0.2°, 8.5°±0.2° and 13.6°±0.2°. Preferably, the X-ray powder diffraction pattern of Form CS5 shows three diffraction peaks at 2theta values of 21.6°±0.2°, 8.5°±0.2° and 13.6°±0.2°.

Furthermore, the X-ray powder diffraction pattern of Form CS5 shows one or two or three diffraction peaks at 2theta values of 13.0°±0.2°, 25.0°±0.2° and 26.0°±0.2°. Preferably, the X-ray powder diffraction pattern of Form CS5 shows three diffraction peaks at 2theta values of 13.0°±0.2°, 25.0°±0.2° and 26.0°±0.2°.

Furthermore, the X-ray powder diffraction pattern of Form CS5 shows characteristic peaks at 2theta values of 4.3°±0.2°, 6.8°±0.2°, 8.5°±0.2°, 13.0°±0.2°, 13.6°±0.2°, 16.4°±0.2°, 21.6°±0.2°, 25.0°±0.2° and 26.0°±0.2°.

In a preferred embodiment, the X-ray powder diffraction pattern of Form CS5 is substantially as depicted in FIG. 10.

In a preferred embodiment, the differential scanning calorimetry (DSC) curve of Form CS5 shows the first endothermic peak when heated to around 65° C., shows an exothermic peak when heated to around 91° C. and shows the second endothermic peak when heated to around 133° C. and which is substantially as depicted in FIG. 11.

Another objective of the present disclosure is to provide the process of preparing Form CS5 of ozanimod. The process comprises adding the solid of ozanimod into cyclic ethers, filtering, evaporating the filtrate and collecting the solid to obtain Form CS5 of ozanimod.

Furthermore, said cyclic ether is 2-methyltetrahydrofuran.

Another objective of the present disclosure is to provide a crystalline form of ozanimod, designated as Form CS6.

The X-ray powder diffraction pattern of Form CS6 shows characteristic peaks at 2theta values of 4.4°±0.2°, 24.5°±0.2°, 26.5°±0.2° and 13.8°±0.2° using CuKα radiation.

Furthermore, the X-ray powder diffraction pattern of Form CS6 shows one or two diffraction peaks at 2theta values of 13.0°±0.2° and 25.4°±0.2°. Preferably, the X-ray powder diffraction pattern of Form CS6 shows two diffraction peaks at 2theta values of 13.0°±0.2° and 25.4°±0.2°.

Furthermore, the X-ray powder diffraction pattern of Form CS6 shows one or two or three diffraction peaks at 2theta values of 8.9°±0.2°, 13.4°±0.2° and 11.0°±0.2°. Preferably, the X-ray powder diffraction pattern of Form CS6 shows three diffraction peaks at 2theta values of 8.9°±0.2°, 13.4°±0.2° and 11.0°±0.2°.

Furthermore, the X-ray powder diffraction pattern of Form CS6 shows characteristic peaks at 2theta values of 4.4°±0.2°, 8.9°±0.2°, 11.0°±0.2°, 13.0°±0.2°, 13.4°±0.2°, 13.8°±0.2°, 24.5°±0.2°, 25.4°±0.2° and 26.5°±0.2°.

In a preferred embodiment, the X-ray powder diffraction pattern of Form CS6 is substantially as depicted in FIG. 16.

In a preferred embodiment, the differential scanning calorimetry (DSC) curve of Form CS6 shows an exothermic peak when heated to around 110° C. and shows an endothermic peak when heated to around 135° C., which is substantially as depicted in FIG. 13.

In a preferred embodiment, the thermal gravimetric analysis (TGA) curve of Form CS6 shows about 1.2% weight loss when heated to 120° C., which is substantially as depicted in FIG. 14.

Another objective of the present disclosure is to provide the process of preparing Form CS6 of ozanimod. The process comprises adding the solid of ozanimod into a solvent selected from ketones, chloroform and the like, filtering, evaporating the filtrate and collecting the solid to obtain Form CS6 of ozanimod.

Preferably, said ketone is acetone.

Another objective of the present disclosure is to provide a pharmaceutical composition comprising a therapeutically amount of ozanimod Form CS1 or Form CS2 or a combination thereof and pharmaceutically acceptable carriers, diluents or excipients. Generally, mix or contact therapeutically a therapeutically amount of Form CS1 or Form CS2 or a combination thereof and one or more pharmaceutically acceptable excipients to make pharmaceutical composition or drug products, and the pharmaceutical composition or drug products are prepared by well-known method in the pharmaceutical field.

Ozanimod Form CS1 or Form CS2 or combinations thereof provided by the present disclosure can be used for preparing drugs for treating autoimmune diseases, particularly used for preparing drug products for treating multiple sclerosis and ulcerative colitis.

The present disclosure also provides a pharmaceutical composition comprising a therapeutically amount of ozanimod Form CS3, Form CS5, Form CS6 or combinations thereof and pharmaceutically acceptable carriers, diluents or excipients. Generally, mix or contact therapeutically an effective amount of Form CS3, Form CS5, Form CS6 or a combination thereof and one or more pharmaceutically acceptable excipients to make pharmaceutical composition or drug products, and the pharmaceutical composition or drug products are prepared by well-known method in the pharmaceutical field.

Ozanimod Form CS3, Form CS5 or Form CS6 or combinations thereof provided by present disclosure can be used for preparing drugs of selective modulator of sphingosine-1-phosphate 1 receptor.

Ozanimod Form CS3, Form CS5 or Form CS6 or combinations thereof provided by present disclosure can be used for preparing drugs for treating autoimmune diseases, particularly used for preparing drug products for treating multiple sclerosis and ulcerative colitis.

The present disclosure further provides a pharmaceutical composition comprising a therapeutically amount of ozanimod Form CS1, Form CS2, Form CS3, Form CS5, Form CS6 or combinations thereof and pharmaceutically acceptable carriers, diluents or excipients.

Furthermore, ozanimod Form CS1, Form CS2, Form CS3, Form CS5, Form CS6 or combinations thereof can be used for preparing drugs of selective modulator of sphingosine-1-phosphate 1 receptor.

Ozanimod Form CS1, Form CS2, Form CS3, Form CS5, Form CS6 or combinations thereof can be used for preparing drugs for treating ulcerative colitis.

Ozanimod Form CS1, Form CS2, Form CS3, Form CS5, Form CS6 or combinations thereof can be used for preparing drugs for treating multiple sclerosis.

Another objective of the present disclosure is to provide a crystalline form of ozanimod hydrochloride, designated as Form CS1 of ozanimod hydrochloride.

The X-ray powder diffraction pattern of Form CS1 of ozanimod hydrochloride shows characteristic peaks at 2theta values of 26.1°±0.2°, 24.4°±0.2° and 20.1°±0.2° using CuKα radiation.

Furthermore, the X-ray powder diffraction pattern of Form CS1 of ozanimod hydrochloride shows one or two or three diffraction peaks at 2theta values of 3.9°±0.2°, 21.1°±0.2° and 7.9°±0.2°. Preferably, the X-ray powder diffraction pattern of Form CS1 of ozanimod hydrochloride shows three diffraction peaks at 2theta values of 3.9°±0.2°, 21.1°±0.2° and 7.9°±0.2°.

Furthermore, the X-ray powder diffraction pattern of Form CS1 of ozanimod hydrochloride shows one or two or three diffraction peaks at 2theta values of 11.9°±0.2°, 19.6°±0.2° and 13.8°±0.2°. Preferably, the X-ray powder diffraction pattern of Form CS1 of ozanimod hydrochloride shows diffraction peaks at 2theta values of 11.9°±0.2°, 19.6°±0.2° and 13.8°±0.2°.

Furthermore, the X-ray powder diffraction pattern of Form CS1 of ozanimod hydrochloride shows characteristic peaks at 2theta values of 3.9°±0.2°, 7.9°±0.2°, 11.9°±0.2°, 13.8°±0.2°, 19.6°±0.2°, 20.1°±0.2°, 21.1°±0.2°, 24.4°±0.2° and 26.1°±0.2°.

In a preferred embodiment, the X-ray powder diffraction pattern of Form CS1 of hydrochloride is substantially as depicted in FIG. 17.

In a preferred embodiment, the X-ray powder diffraction pattern of Form CS1 of hydrochloride is substantially as depicted in FIG. 20.

In a preferred embodiment, the differential scanning calorimetry (DSC) curve of Form CS1 of hydrochloride shows an endothermic peak when heated to around 238° C., which is substantially as depicted in FIG. 18.

In a preferred embodiment, the thermal gravimetric analysis (TGA) curve of Form CS1 of hydrochloride shows about 1.1% weight loss when heated to 150° C., which is substantially as depicted in FIG. 19.

Another objective of the present disclosure is to provide the process of preparing Form CS1 of ozanimod hydrochloride. The process comprises method 1) or method 2) or method 3) or method 4), 1) Adding ozanimod hydrochloride into ethers and stirring for a period of time at a certain temperature (4-50° C., preferably 25° C.), filtering and drying to obtain white solid; said stirring time is at least 1 hour, preferably at least 24 hours, more preferably seven days; or 2) Dissolving ozanimod hydrochloride into a solvent selected from alcohols and esters or a mixture of solvents thereof, evaporating at room temperature to obtain white solid; said "evaporation time" usually means the time or longer than the time for solid precipitation. The evaporation time is preferably 0.5 day to 14 days, more preferably 7 days; or 3) Dissolving ozanimod hydrochloride into a solvent selected from amides or a mixture of solvents thereof, then placing the solution in a system containing anti-solvent of ozanimod hydrochloride for liquid vapor diffusion at room temperature, filtering and drying to obtain white solid; said "diffusion time" usually means the time or longer than the time for solid precipitation. The diffusion time is preferably 1 day to 14 days, more preferably 7 days; or 4) Dissolving ozanimod hydrochloride into a mixture of alcohols and water to form a supersaturated solution, ozanimod hydrochloride is fully dissolved at 25-80° C. (preferably 50° C.), and then filtering, cooling the filtrate for precipitation, filtering and drying to obtain white solid of Form CS1 of ozanimod hydrochloride.

Another objective of the present disclosure is to provide a pharmaceutical composition comprising a therapeutically amount of Form CS1 of ozanimod hydrochloride and pharmaceutically acceptable carriers, diluents or excipients. Generally, mix or contact therapeutically an effective amount of Form CS1 of ozanimod hydrochloride and one or more pharmaceutically acceptable excipients to make pharmaceutical composition or drug products, and the pharmaceutical composition or drug products are prepared by well-known method in the pharmaceutical field.

Furthermore, Form CS1 of ozanimod hydrochloride provided by present disclosure can be used for preparing drugs for treating autoimmune diseases, particularly used for preparing drug products for treating multiple sclerosis and ulcerative colitis.

Said "room temperature" in the present disclosure is not an exact temperature value and refers to 10-30° C.

The reaction time of "evaporating" and "diffusion" in the present disclosure refers to the time before solid precipitation or longer.

Said "stirring" is accomplished by using a conventional method in the field such as a magnetic stirring or a mechanical stirring and the stirring speed is 50 to 1800 r/min, preferably is 300 to 900 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished at room temperature or a higher temperature. The drying temperature is from room temperature to about 60° C., or to 40° C., or to 50° C. The drying time can be 2 to 48 hours, or overnight. Drying is accomplished in a fume hood, oven or vacuum oven.

Said "evaporating" is accomplished by using a conventional method in the field. For example, slow evaporation is to seal the container with a sealing film and puncture holes for evaporation. Rapid evaporation is to place the container open for evaporation.

Said "polymer" is a mixture of equal masses of polycaprolactone, polyoxyethylene, polymethyl methacrylate, sodium alginate, and hydroxyethyl cellulose.

The beneficial effects of the present disclosure are as follows:

At present, no patent or literature has disclosed the crystalline form of ozanimod and inventors of the present disclosure broke through this difficult problem and several novel crystalline forms of ozanimod suitable for the drug development are found.

The crystalline forms and crystalline form of hydrochloride provided by the present disclosure have advantages in solubility, melting point, stability, dissolution, bioavailability and processability. As for the crystalline Form CS1, Form CS2, Form CS3, Form CS5, Form CS6 and Form CS1 of the hydrochloride, the hygroscopicity is low, stability is good, solubility meets the medicinal requirements, particle size distribution is uniform and the dispersion is good. These advantages help to simplify the post-treatment process of preparing drugs and provide new and better choices for the preparation of ozanimod drug products, which are very important for drug development.

DETAILED DESCRIPTION OF THE DISCLOSURE

Figure 1:
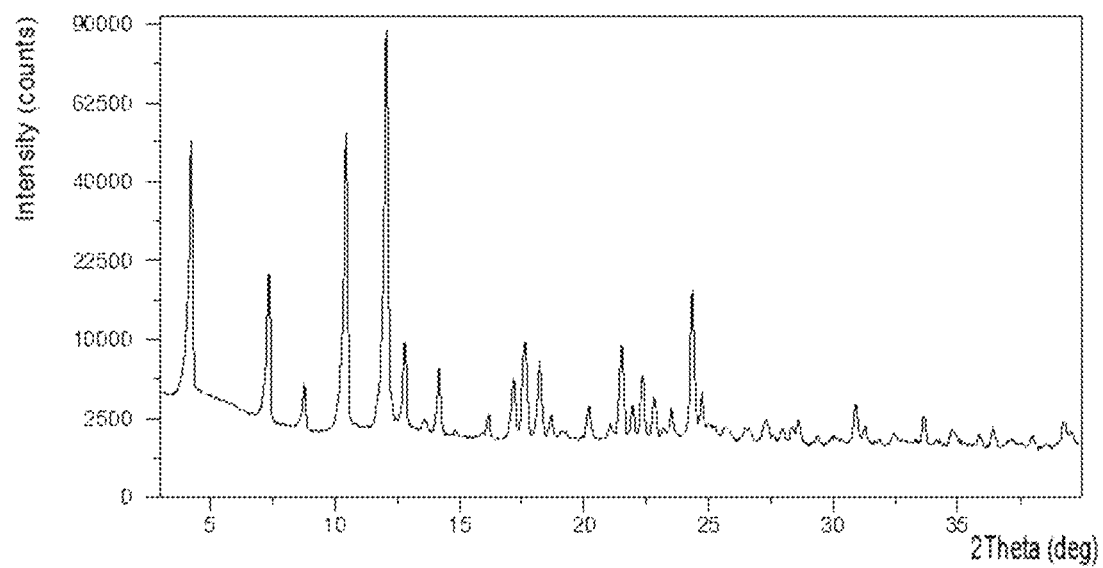
FIG. 1 shows an XRPD pattern of Form CS1 obtained in Example 1.

The present disclosure is further illustrated by the following examples in detail, but is not intended to limit the scope of the present disclosure. The skilled in the art can make improvements to the process of preparation and the instruments used within the scope of the claims, and those improvements should be considered as falling into the scope of the present disclosure. Therefore, the protective scope of the present disclosure patent should be defined by the claims.

In the following examples, the test method is generally implemented according to a conventional condition or a condition recommended by manufacturer.

The abbreviations used in the disclosure are explained as follows:
XRPD: X-ray Powder Diffraction
DSC: Differential Scanning calorimetry
TGA: Thermal Gravimetric Analysis DVS: Dynamic Vapor Sorption
PSD: Particle Size Distribution
PLM: Polarized Light microscopy X-ray powder diffraction pattern in the present disclosure was acquired by a Panalytical Empyrean X-ray powder diffractometer. The parameters of the X-ray powder diffraction method of the present disclosure were as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure were acquired by a TA Q2000. The parameters of the differential scanning calorimetry (DSC) method of the present disclosure were as follow:
Heating rate: 10° C./min
Purge gas: nitrogen Thermal gravimetric analysis (TGA) data in the present disclosure were acquired by a TA Q5000. The parameters of the thermal gravimetric analysis (TGA) method of the present disclosure were as follow:
Heating rate: 10° C./min
Purge gas: nitrogen Dynamic Vapor Sorption (DVS) is measured via an SMS (Surface Measurement Systems Ltd.) intrinsic DVS. Typical Parameters for DVS test are as follows:
Temperature: 25° C.
Gas and flow rate: N$_2$, 200 mL/min
dm/dt: 0.002%/min
RH range: 0% RH to 95% RH The particle size distribution test in the present disclosure is acquired by the S3500 laser particle size analyzer of Microtrac. Microtrac S3500 is equipped with the SDC (Sample Delivery Controller). The test is carried out by wet process, and the dispersion medium is Isopar G The parameters are as follow:

| | |
|---|---|
| Size distribution: Volume | Run Time: 10 s |
| Dispersion medium: Isopar G | Particle coordinates: Standard |
| Run Number: Average of 3 runs | Fluid refractive index: 1.42 |
| Particle Transparency:: Trans | Residuals: Enabled |
| Particle refractive index: 1.5 | Flow rate: 60%* |
| Particle shape: Irregular | Filtration: Enabled |
| Ultrasonication power: 30 W | Ultrasonication time: 30 s |

*Flow rate 60% is 60% of 65 mL/s.

Raw materials of ozanimod and/or a hydrochloride thereof used in the following examples are prepared by methods disclosed in CN102762100A.

Example 1

Preparation of Form CS1 of Ozanimod:
About 2.0 g of ozanimod hydrochloride was added into a 150-mL glass vial followed by adding 100 mL of methanol to form a suspension at room temperature. The suspension became clear after 7.0 mL of sodium hydroxide solution (32 mg/mL) was added dropwise. And then, white solid precipitated out after stirring at room temperature for 12 hours. The suspension was centrifuged and dried to isolate solid.

Figure 2:
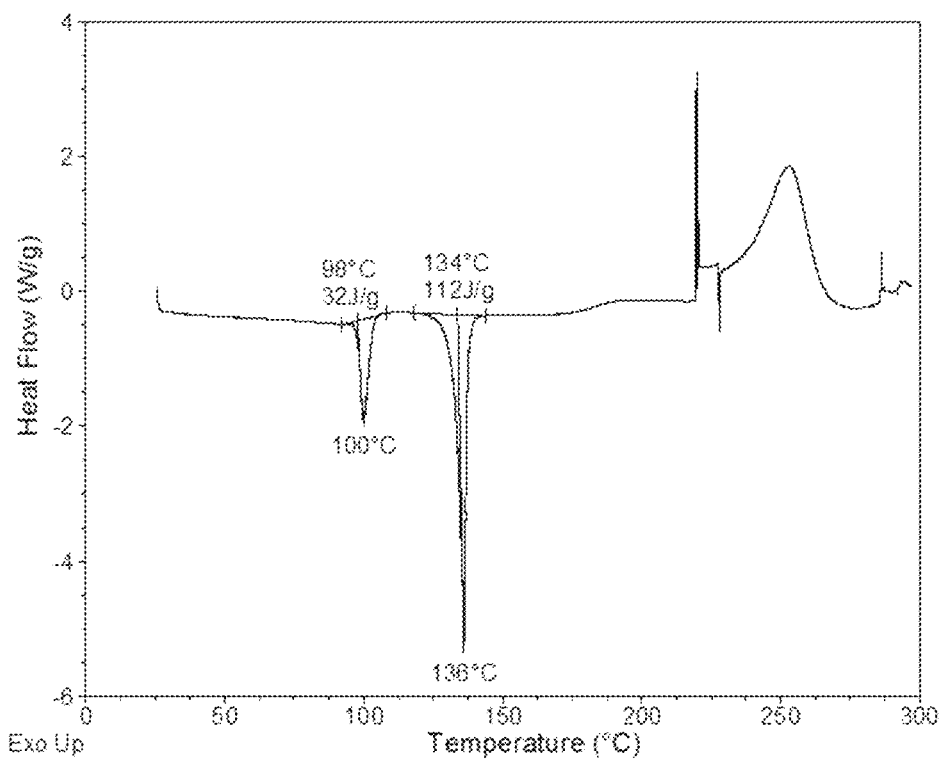
FIG. 2 shows a DSC curve of Form CS1 obtained in Example 1.
Figure 3:
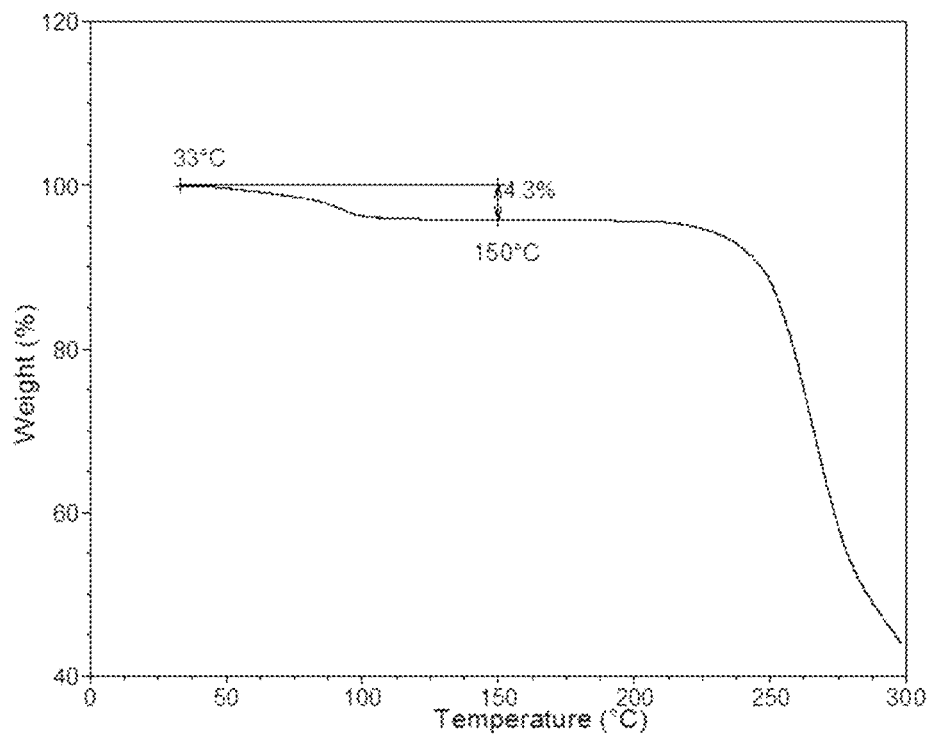
FIG. 3 shows a TGA curve of Form CS1 obtained in Example 1.

The obtained solid was identified as Form CS1. The XRPD data of the solid prepared in this example are listed in Table 1. The XRPD pattern is displayed in FIG. 1. The DSC curve is displayed in FIG. 2. The TGA curve is displayed in FIG. 3.

TABLE 1

| 2theta | d spacing | Relative intensity % |
|---|---|---|
| 4.24 | 20.83 | 53.60 |
| 7.37 | 12.00 | 20.87 |
| 8.78 | 10.07 | 3.91 |
| 10.45 | 8.46 | 60.36 |
| 12.07 | 7.33 | 100.00 |
| 12.82 | 6.90 | 9.66 |
| 14.19 | 6.24 | 6.17 |
| 16.17 | 5.48 | 1.63 |
| 17.19 | 5.16 | 4.96 |
| 17.65 | 5.02 | 9.86 |
| 18.22 | 4.87 | 7.35 |
| 18.69 | 4.75 | 1.61 |
| 20.18 | 4.40 | 2.40 |
| 21.51 | 4.13 | 9.64 |
| 21.95 | 4.05 | 2.44 |
| 22.35 | 3.98 | 5.65 |
| 22.82 | 3.90 | 3.25 |
| 23.51 | 3.78 | 2.32 |
| 24.35 | 3.66 | 19.15 |
| 24.74 | 3.60 | 3.72 |
| 25.69 | 3.47 | 0.86 |
| 26.63 | 3.35 | 0.75 |
| 27.30 | 3.27 | 1.49 |
| 28.60 | 3.12 | 1.52 |
| 30.90 | 2.89 | 2.80 |
| 31.26 | 2.86 | 1.01 |
| 32.44 | 2.76 | 0.57 |
| 33.63 | 2.67 | 1.87 |
| 34.77 | 2.58 | 0.91 |
| 36.41 | 2.47 | 1.13 |
| 39.25 | 2.30 | 1.49 |

Use the preparation method of example 1, about 10 mg of ozanimod hydrochloride was suspended in methanol, acetone, isopropyl acetate or acetonitrile. The suspension became clear after 1.0-1.5 equivalent of sodium hydroxide solution was added. Then white solid precipitated out after stirring the solution at room temperature for 12 hours. The suspension was centrifuged to obtain solid. The solid was dried under vacuum. The obtained solid was identified as Form CS1 and its XRPD pattern was same as FIG. 1.

Example 2

Preparation of Form CS1 of Ozanimod:
About 10 mg of ozanimod and 0.5 mL of methanol was added into a 1.5-mL glass vial. The suspension was stirred at room temperature for 24 hours. The obtained white solid was identified as Form CS1 and its XRPD pattern was substantially the same as FIG. 1.

Example 3

Preparation of Form CS2 of ozanimod:
About 20 mg of Form CS1 of ozanimod was added into a 3-mL glass vial. And then, the solid was dried under vacuum at 110° C. for 1 hour. The obtained white solid was identified as Form CS2.

Figure 4:
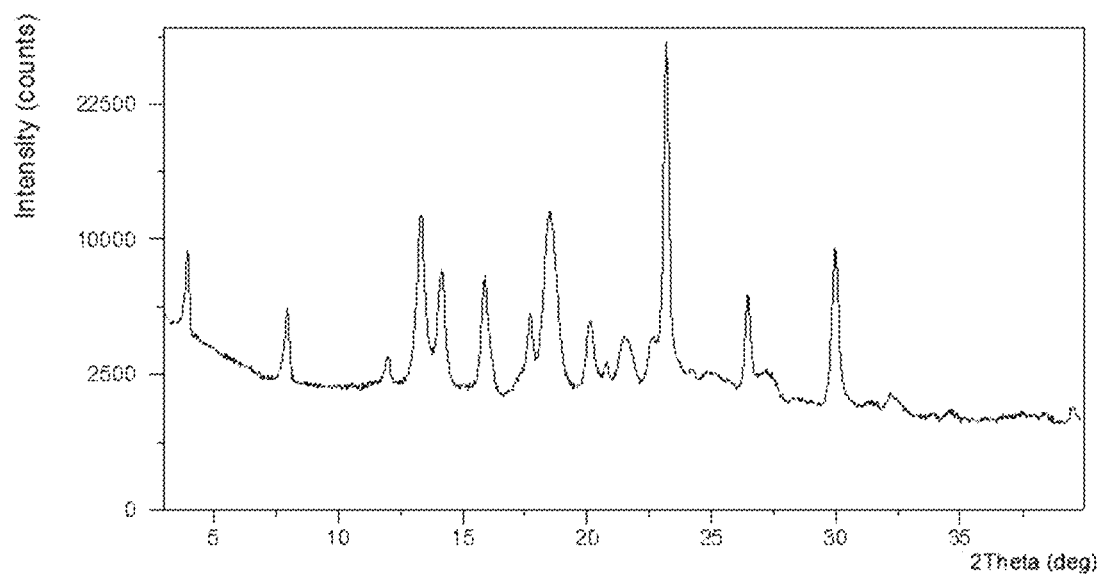
FIG. 4 shows an XRPD pattern of Form CS2 obtained in Example 3.
Figure 5:
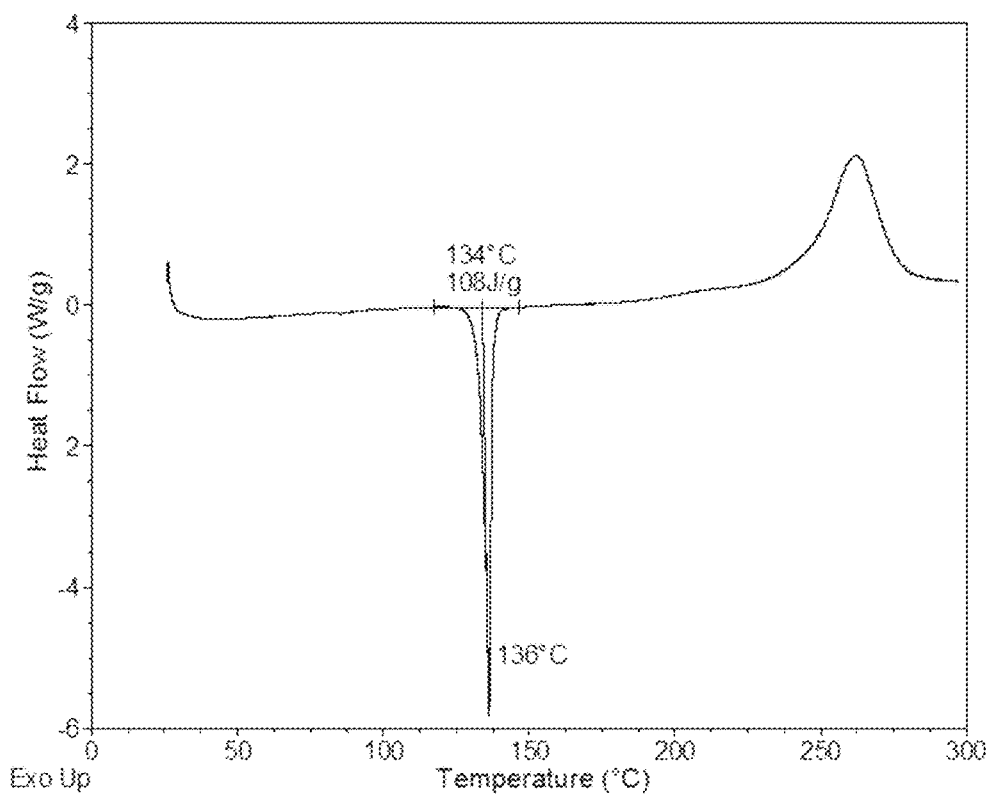
FIG. 5 shows a DSC curve of Form CS2 obtained in Example 3.
Figure 6:
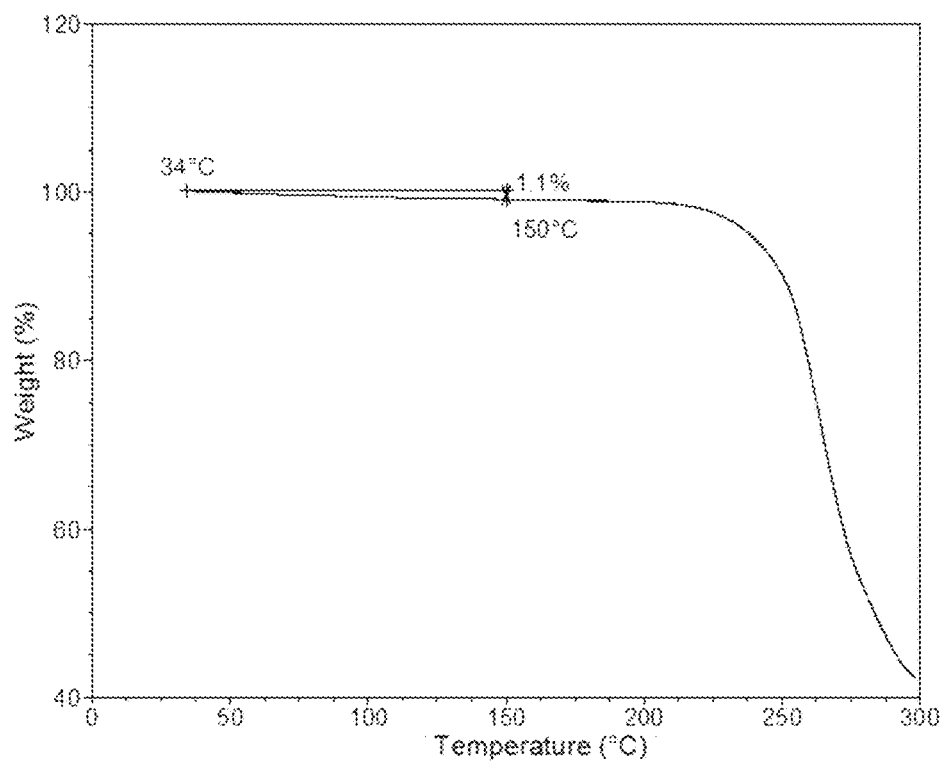
FIG. 6 shows a TGA curve of Form CS2 obtained in Example 3.

The XRPD data of the solid prepared in this example are listed in Table 2. The XRPD pattern is displayed in FIG. 4. The DSC curve is displayed in FIG. 5. The TGA curve is displayed in FIG. 6.

TABLE 2

| 2theta | d spacing | Relative intensity % |
|---|---|---|
| 3.96 | 22.33 | 20.48 |
| 7.95 | 11.12 | 11.39 |

TABLE 2-continued

| 2theta | d spacing | Relative intensity % |
|---|---|---|
| 12.02 | 7.36 | 4.10 |
| 13.33 | 6.64 | 35.96 |
| 14.16 | 6.25 | 21.29 |
| 15.89 | 5.58 | 19.75 |
| 17.72 | 5.00 | 12.52 |
| 18.49 | 4.80 | 36.64 |
| 20.08 | 4.42 | 11.25 |
| 20.77 | 4.28 | 4.59 |
| 21.36 | 4.16 | 7.46 |
| 21.53 | 4.13 | 8.77 |
| 22.56 | 3.94 | 8.50 |
| 23.19 | 3.84 | 100.00 |
| 24.22 | 3.67 | 4.08 |
| 24.97 | 3.57 | 3.68 |
| 26.47 | 3.37 | 17.30 |
| 27.46 | 3.25 | 3.66 |
| 28.40 | 3.14 | 1.16 |
| 29.98 | 2.98 | 28.43 |
| 31.45 | 2.84 | 1.01 |
| 32.19 | 2.78 | 2.21 |
| 34.53 | 2.60 | 0.69 |
| 37.45 | 2.40 | 0.61 |
| 38.43 | 2.34 | 0.73 |
| 39.50 | 2.28 | 1.41 |

Example 4A-4j

Preparation of Form CS2 of Ozanimod:

As shown in Table 3, about 10 mg of ozanimod was added into 1.5-mL galss vials followed by adding a certain volume of solvents to form suspensions. These suspensions were stirred at room temperature for 24 hours. The obtained solids were collected and labeled as samples 1-10. Samples 1-10 were identified as Form CS2. The X-ray powder diffraction patterns of these samples are same as FIG. 4, which shows characteristic peaks at 2theta values of 4.0°±0.2°, 13.3°±0.2°, 14.2°±0.2°, 15.9°±0.2°, 17.7°±0.2°, 18.5°±0.2°, 23.2°±0.2°, 26.5°±0.2° and 30.0°±0.2°.

TABLE 3

| Example | Mass (mg) | Solvent | Volume (mL) | Solid Form | Label |
|---|---|---|---|---|---|
| 4a | 10.2 | Acetonitrile | 0.5 | CS2 | Sample 1 |
| 4b | 10.3 | Acetone | 0.5 | CS2 | Sample 2 |
| 4c | 10.3 | Methyl isobutyl ketone | 0.5 | CS2 | Sample 3 |
| 4d | 10.8 | Ethyl acetate | 0.5 | CS2 | Sample 4 |
| 4e | 9.8 | Toluene | 0.5 | CS2 | Sample 5 |
| 4f | 9.7 | 2-Methyltetrahydrofuran | 0.5 | CS2 | Sample 6 |
| 4g | 10.0 | Water | 0.5 | CS2 | Sample 7 |
| 4h | 10.4 | Ethanol/water (19:1, v/v) | 0.5 | CS2 | Sample 8 |
| 4i | 9.4 | Dimethylformamide/water (3:2, v/v) | 0.5 | CS2 | Sample 9 |
| 4j | 9.7 | Acetone/water (9:1, v/v) | 0.5 | CS2 | Sample 10 |

Example 5

Preparation of Form CS3 of Ozanimod:

About 5.0 mg of ozanimod was added into a 3-mL galss vial followed by adding 0.4 mL of dichloromethane. The mixture was filtered and about 0.2 mg of polymer was added into the clear solution. And then the solution was slowly evaporated at room temperature until white solid was obtained. The obtained white solid was identified as Form CS3.

Figure 7:
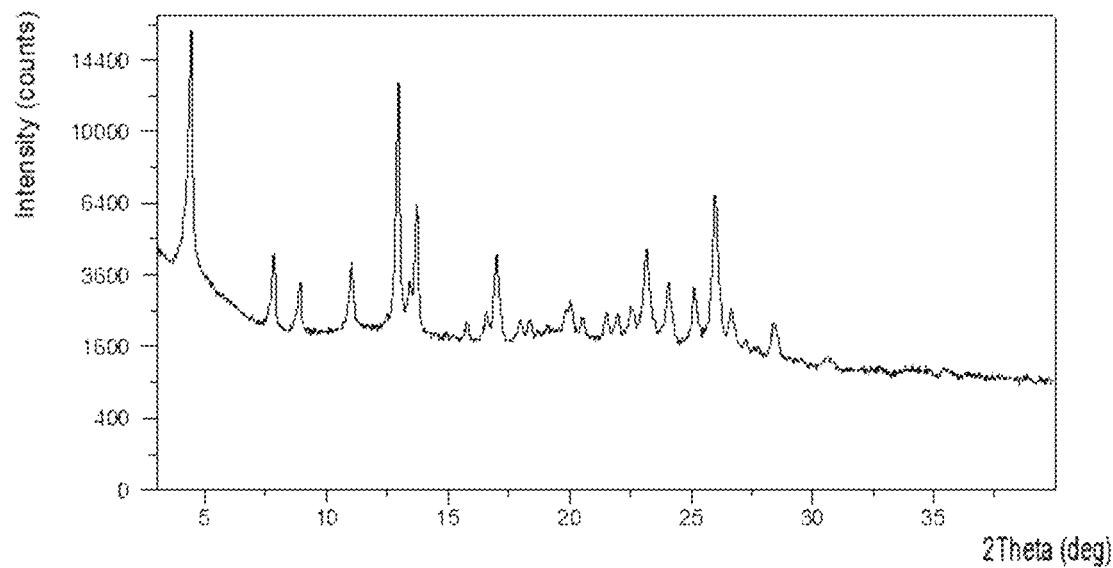
FIG. 7 shows an XRPD pattern of Form CS3 obtained in Example 5.
Figure 8:
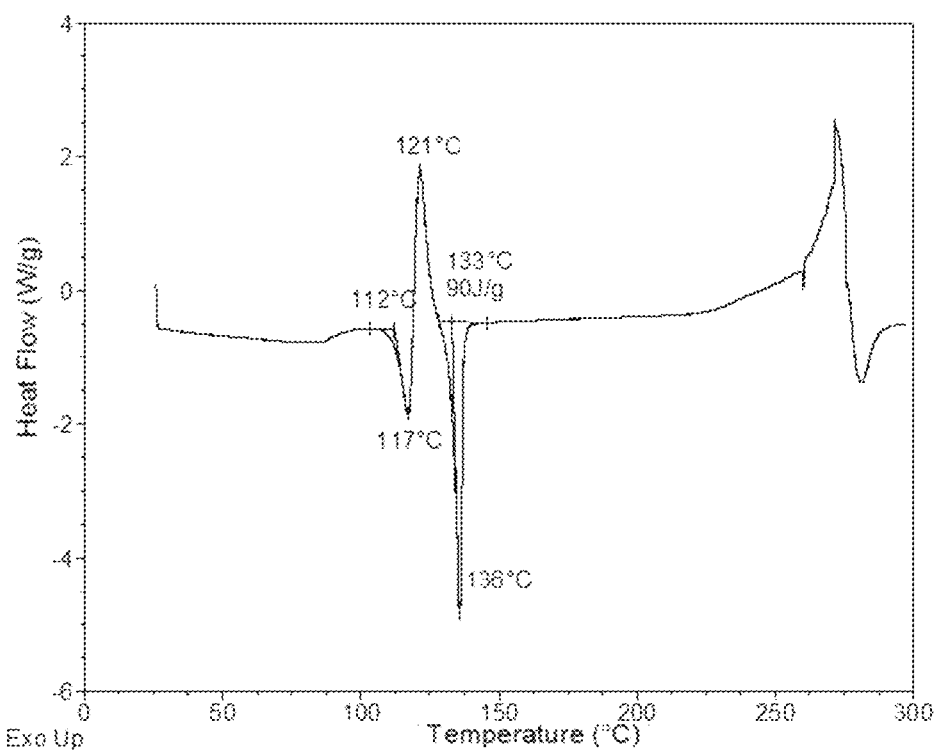
FIG. 8 shows a DSC curve of Form CS3 obtained in Example 5.
Figure 9:
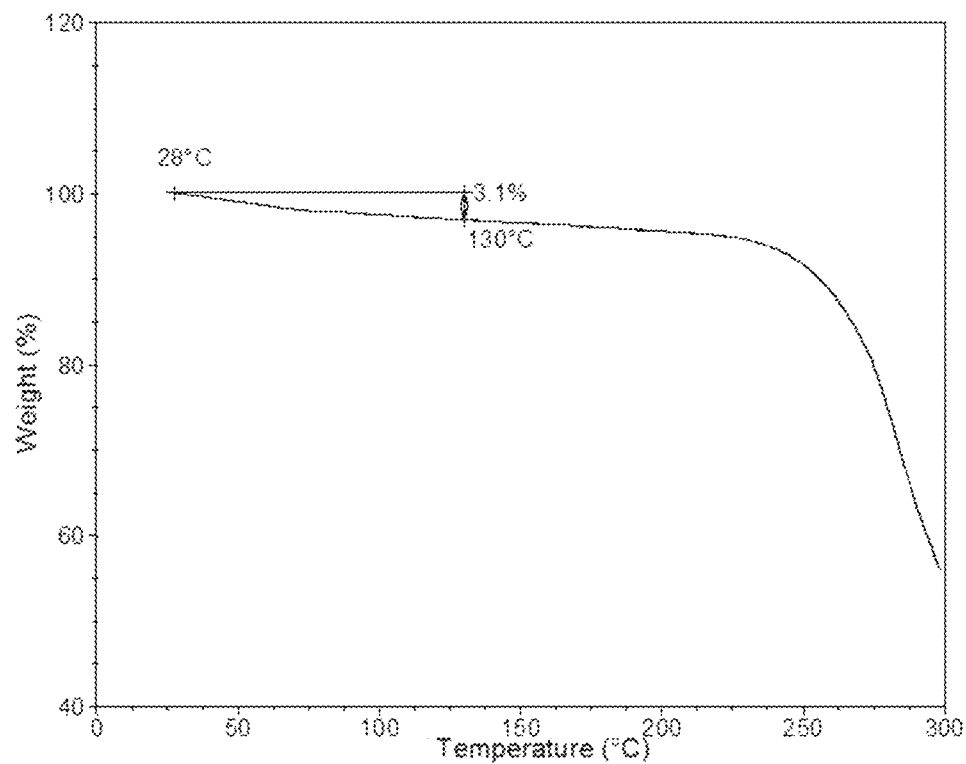
FIG. 9 shows a TGA curve of Form CS3 obtained in Example 5.

The XRPD data of the solid prepared in this example are listed in Table 4. The XRPD pattern is displayed in FIG. 7. The DSC curve is displayed in FIG. 8. The TGA curve is displayed in FIG. 9.

TABLE 4

| 2theta | d spacing | Relatively intensity % |
|---|---|---|
| 3.04 | 29.02 | 12.88 |
| 4.43 | 19.93 | 100.00 |
| 7.84 | 11.28 | 16.58 |
| 8.92 | 9.92 | 10.16 |
| 11.03 | 8.02 | 15.96 |
| 12.96 | 6.83 | 83.06 |
| 13.43 | 6.59 | 11.89 |
| 13.72 | 6.46 | 33.05 |
| 15.80 | 5.61 | 3.44 |
| 16.57 | 5.35 | 5.55 |
| 17.00 | 5.21 | 19.94 |
| 17.98 | 4.93 | 4.44 |
| 18.38 | 4.83 | 4.34 |
| 19.83 | 4.48 | 6.93 |
| 20.06 | 4.43 | 8.40 |
| 20.57 | 4.32 | 5.85 |
| 21.53 | 4.13 | 7.15 |
| 21.98 | 4.04 | 6.11 |
| 22.56 | 3.94 | 8.12 |
| 23.17 | 3.84 | 23.33 |
| 24.09 | 3.69 | 14.77 |
| 25.14 | 3.54 | 12.77 |
| 26.00 | 3.43 | 41.57 |
| 26.68 | 3.34 | 9.46 |
| 28.42 | 3.14 | 6.82 |
| 30.67 | 2.91 | 1.27 |
| 33.98 | 2.64 | 0.53 |
| 35.51 | 2.53 | 0.79 |

Example 6

Preparation of Form CS3 of Ozanimod:

About 5 mg of ozanimod solid was added into a 3-mL galss vial followed by adding 1.0 mL of acetonitrile. The mixture was filtered and fast evaporated at room temperature until white solid was obtained.

Figure 15:
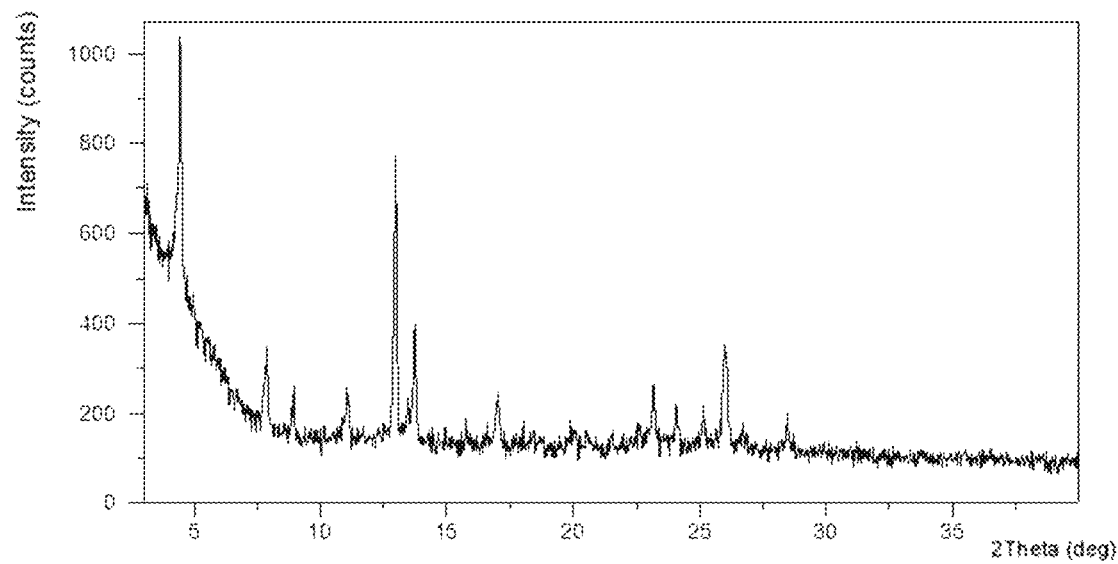
FIG. 15 shows an XRPD pattern of Form CS3 obtained in Example 6.

The obtained white solid was identified as Form CS3. The XRPD data of the solid prepared in this example are listed in Table 5. The XRPD pattern is displayed in FIG. 15.

TABLE 5

| 2theta | d spacing | Relatively intensity % |
|---|---|---|
| 4.44 | 19.89 | 94.06 |
| 5.20 | 16.98 | 3.53 |
| 7.86 | 11.25 | 22.55 |
| 8.93 | 9.90 | 15.72 |
| 9.38 | 9.433 | 4.17 |
| 11.05 | 8.00 | 18.33 |
| 12.97 | 6.83 | 100.00 |
| 13.73 | 6.45 | 41.96 |
| 14.44 | 6.13 | 7.95 |
| 15.78 | 5.62 | 8.10 |
| 16.14 | 5.49 | 4.53 |
| 17.01 | 5.21 | 19.74 |
| 18.22 | 4.87 | 2.42 |
| 20.07 | 4.42 | 8.54 |
| 20.26 | 4.39 | 3.28 |
| 20.50 | 4.34 | 6.66 |
| 21.53 | 4.13 | 7.83 |
| 21.99 | 4.04 | 4.91 |
| 22.60 | 3.93 | 11.03 |
| 23.18 | 3.84 | 24.17 |
| 24.08 | 3.70 | 14.26 |

TABLE 5-continued

| 2theta | d spacing | Relatively intensity % |
|---|---|---|
| 25.15 | 3.54 | 11.64 |
| 26.03 | 3.42 | 39.79 |
| 26.63 | 3.35 | 5.94 |
| 28.42 | 3.14 | 12.28 |
| 30.39 | 2.94 | 4.29 |
| 37.15 | 2.42 | 5.92 |
| 37.37 | 2.41 | 4.67 |

Use the preparation method of example 6, Form CS3 can be prepared by evaporation in methanol, isopropyl acetate and dimethyl sulfoxide.

Example 7

Preparation of Form CS3 of Ozanimod:
About 15 mg of ozanimod solid was added into a 3-mL galss vial followed by adding 1.0 mL of solvent mixture of glycol dimethyl ether and water (1:1, v/v). The mixture was filtered and slowly evaporated at room temperature until white solid was obtained.

Figure 53:
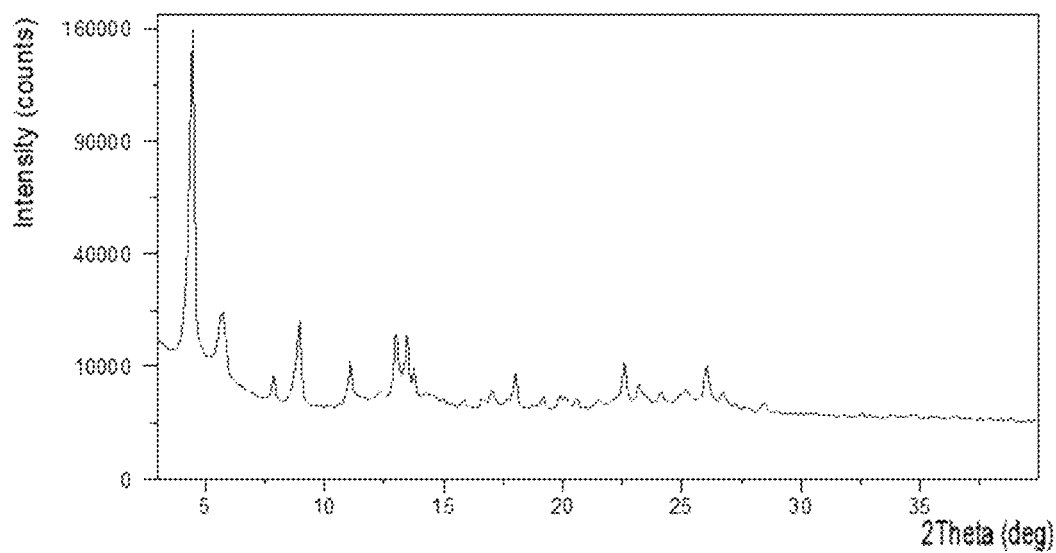
FIG. 53 shows an XRPD pattern of Form CS3 in Example 7.

The obtained white solid was identified as Form CS3, which shows characteristic peaks at 2theta values of 4.42°, 5.70°, 7.85°, 11.06°, 12.99°, 17.04°, 23.21°, 24.11° and 26.04°. The XRPD pattern is displayed in FIG. 53.

Example 8

Preparation of Form CS5 of Ozanimod:
About 10 mg of ozanimod solid was added into a 3-mL galss vial followed by adding 2.4 mL of 2-methyltetrahydrofuran. The mixture was filtered and fast evaporated at room temperature to obtain white solid.

Figure 10:
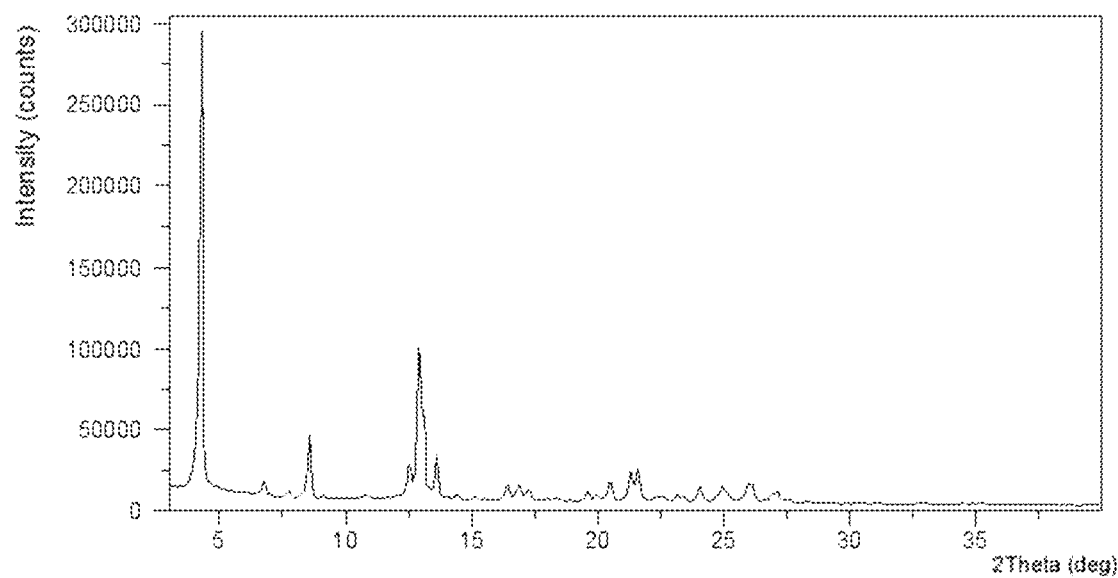
FIG. 10 shows an XRPD pattern of Form CS5 obtained in Example 8.
Figure 11:
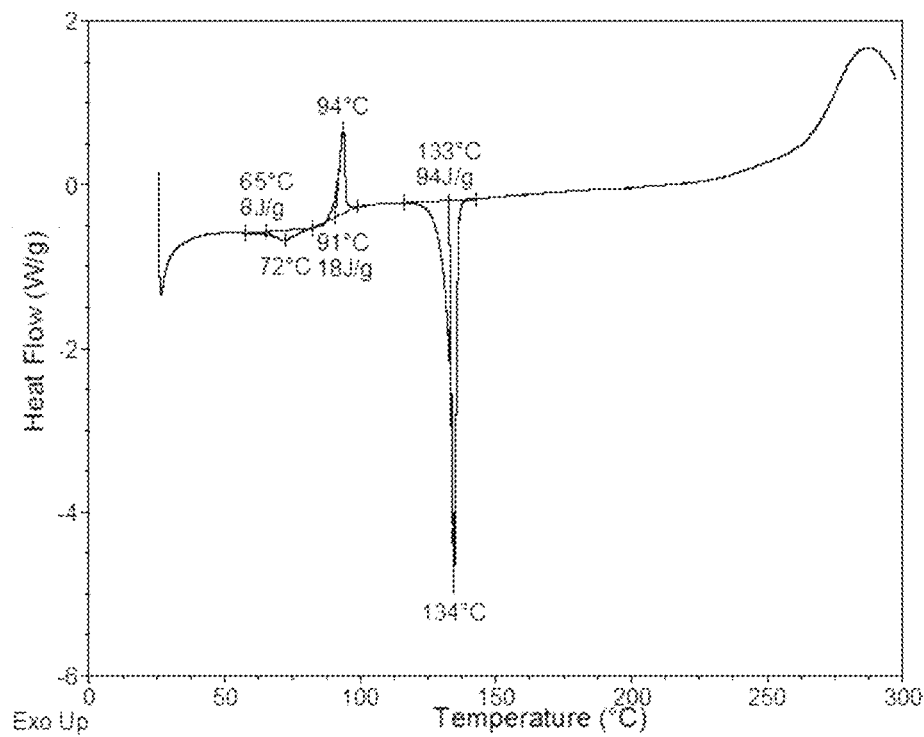
FIG. 11 shows a DSC curve of Form CS5 obtained in Example 8.

The obtained white solid was identified as Form CS5. The XRPD data of the solid prepared in this example are listed in Table 6. The XRPD pattern is displayed in FIG. 10. The DSC curve is displayed in FIG. 11.

TABLE 6

| 2theta | d spacing | Relatively intensity % |
|---|---|---|
| 4.25 | 20.80 | 100.00 |
| 6.76 | 13.08 | 3.43 |
| 7.71 | 11.47 | 1.36 |
| 8.55 | 10.34 | 13.99 |
| 10.79 | 8.20 | 1.07 |
| 12.96 | 6.83 | 34.38 |
| 13.61 | 6.51 | 9.98 |
| 14.42 | 6.14 | 1.40 |
| 15.13 | 5.85 | 1.00 |
| 16.39 | 5.41 | 3.84 |
| 16.86 | 5.26 | 4.05 |
| 17.29 | 5.13 | 2.70 |
| 18.37 | 4.83 | 0.78 |
| 19.57 | 4.54 | 2.18 |
| 20.48 | 4.34 | 5.14 |
| 21.60 | 4.12 | 8.34 |
| 22.52 | 3.95 | 1.56 |
| 23.20 | 3.83 | 1.88 |
| 24.04 | 3.70 | 4.04 |
| 24.98 | 3.56 | 4.18 |
| 26.03 | 3.42 | 5.50 |
| 27.06 | 3.30 | 3.14 |
| 28.35 | 3.15 | 0.64 |
| 29.00 | 3.08 | 0.35 |
| 30.27 | 2.95 | 0.47 |
| 31.14 | 2.87 | 0.58 |
| 32.77 | 2.73 | 0.49 |

TABLE 6-continued

| 2theta | d spacing | Relatively intensity % |
|---|---|---|
| 35.24 | 2.55 | 0.49 |
| 37.31 | 2.41 | 0.16 |

Example 9

Preparation of Form CS6 of Ozanimod:
About 15 mg of ozanimod was weighed into a 3-mL galss vial followed by adding about 0.2 mL of chloroform. The mixture was filtered and fast evaporated at room temperature to obtain white solid.

Figure 12:
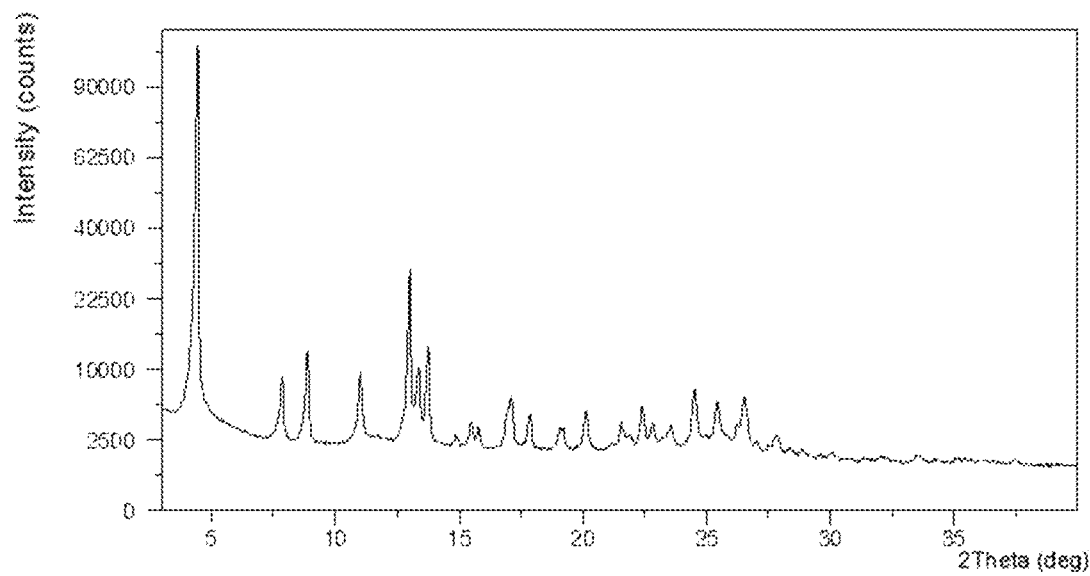
FIG. 12 shows an XRPD pattern of Form CS6 obtained in Example 9.

The obtained white solid was identified as Form CS6. The XRPD data of the solid prepared in this example are listed in Table 7. The XRPD pattern is displayed in FIG. 12.

TABLE 7

| 2theta | d spacing | Relatively intensity % |
|---|---|---|
| 4.45 | 19.88 | 100.00 |
| 7.86 | 11.24 | 6.23 |
| 8.89 | 9.95 | 10.03 |
| 11.03 | 8.02 | 7.43 |
| 13.01 | 6.81 | 26.15 |
| 13.37 | 6.62 | 8.34 |
| 13.75 | 6.44 | 11.19 |
| 14.89 | 5.95 | 0.81 |
| 15.49 | 5.72 | 1.94 |
| 15.79 | 5.61 | 1.52 |
| 16.94 | 5.23 | 3.00 |
| 17.12 | 5.18 | 4.44 |
| 17.87 | 4.96 | 2.72 |
| 19.06 | 4.66 | 1.52 |
| 19.22 | 4.62 | 1.51 |
| 20.13 | 4.41 | 3.22 |
| 21.55 | 4.12 | 2.16 |
| 22.40 | 3.97 | 3.75 |
| 22.82 | 3.90 | 2.11 |
| 23.58 | 3.77 | 2.04 |
| 24.51 | 3.63 | 5.93 |
| 25.42 | 3.50 | 4.55 |
| 26.22 | 3.40 | 2.19 |
| 26.52 | 3.36 | 5.03 |
| 27.06 | 3.30 | 0.91 |
| 27.86 | 3.20 | 1.37 |
| 28.32 | 3.15 | 0.61 |
| 28.86 | 3.09 | 0.51 |
| 30.04 | 2.97 | 0.34 |
| 32.15 | 2.78 | 0.22 |
| 33.55 | 2.67 | 0.33 |
| 37.44 | 2.40 | 0.25 |

Using the preparation method of example 9, Form CS6 can be prepared by evaporating in acetone.

Example 10

Preparation of Form CS6 of Ozanimod:
About 5 mg of ozanimod solid was added into a 3-mL galss vial followed by adding 0.4 mL of chloroform. The mixture was filtered and fast evaporated at room temperature to obtain white solid.

Figure 16:
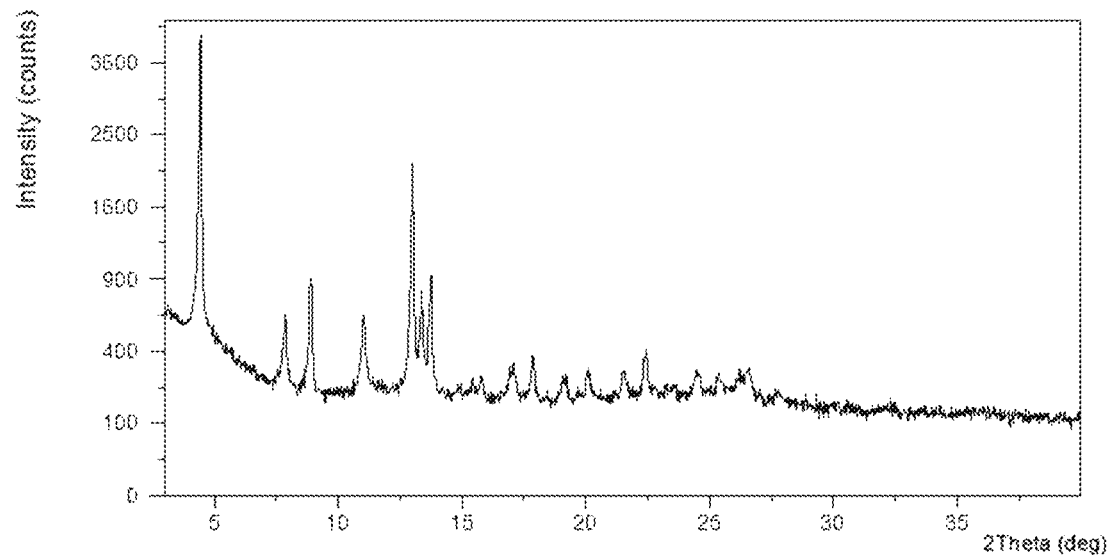
FIG. 16 shows an XRPD pattern of Form CS6 obtained in Example 10.
Figure 17:
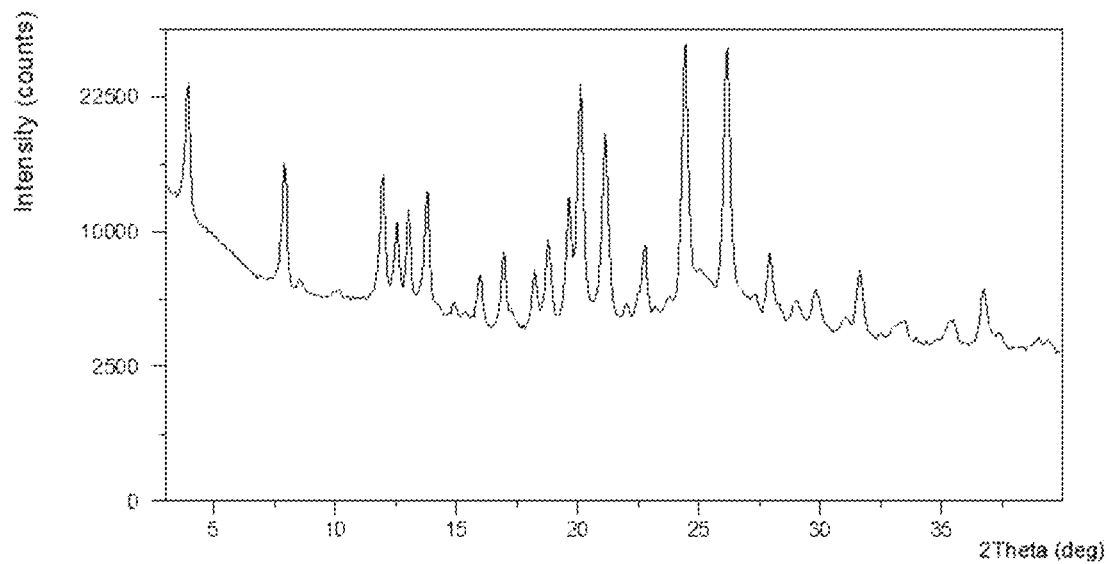
FIG. 17 shows an XRPD pattern of Form CS1 of hydrochloride.

The obtained white solid was identified as Form CS6. The XRPD data of the solid prepared in this example are listed in Table 8. The XRPD pattern is displayed in FIG. 16.

Figure 13:
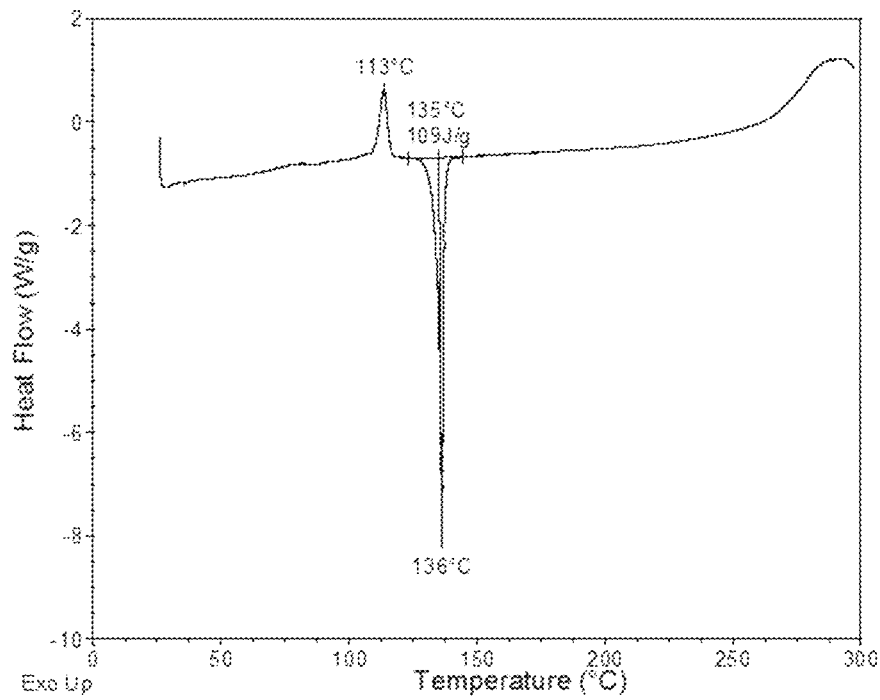
FIG. 13 shows a DSC curve of Form CS6 obtained in Example 10.
Figure 14:
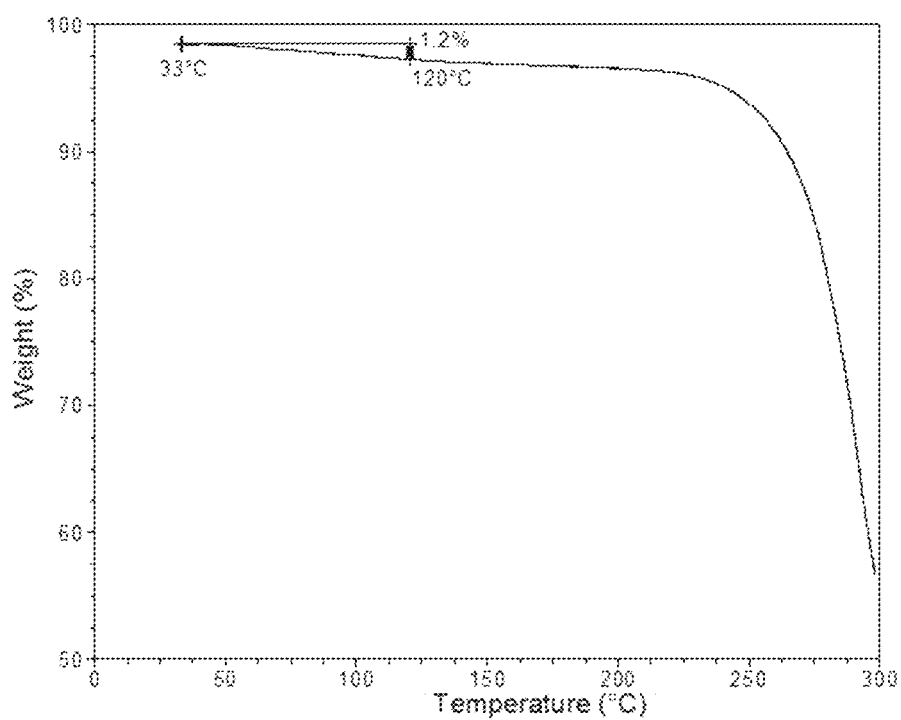
FIG. 14 shows a TGA curve of Form CS6 obtained in Example 10.

10 mg of CS6 was re-prepared using the method of example 10, which was used for DSC and TGA characterization. The DSC curve is displayed in FIG. 13. The TGA curve is displayed in FIG. 14.

TABLE 8

| 2theta | d spacing | Relatively intensity % |
|---|---|---|
| 4.44 | 19.88 | 100.00 |
| 7.86 | 11.25 | 11.49 |
| 8.89 | 9.94 | 19.71 |
| 11.03 | 8.02 | 12.60 |
| 13.00 | 6.81 | 53.68 |
| 13.37 | 6.62 | 15.73 |
| 13.75 | 6.44 | 21.24 |
| 14.95 | 5.93 | 2.05 |
| 15.44 | 5.74 | 2.80 |
| 15.78 | 5.62 | 1.84 |
| 17.08 | 5.19 | 4.53 |
| 17.87 | 4.96 | 5.38 |
| 19.11 | 4.64 | 2.07 |
| 20.06 | 4.43 | 4.31 |
| 21.55 | 4.12 | 4.26 |
| 22.43 | 3.96 | 6.47 |
| 23.44 | 3.80 | 1.73 |
| 24.51 | 3.63 | 3.95 |
| 25.34 | 3.51 | 3.19 |
| 26.18 | 3.40 | 3.93 |
| 26.61 | 3.35 | 4.89 |
| 27.75 | 3.22 | 1.62 |
| 28.94 | 3.09 | 1.01 |
| 30.18 | 2.96 | 0.66 |
| 32.42 | 2.76 | 0.81 |
| 36.51 | 2.46 | 0.47 |
| 37.42 | 2.40 | 0.33 |
| 38.94 | 2.31 | 0.76 |
| 39.35 | 2.29 | 0.61 |

Example 11

Preparation of Form CS1 of Ozanimod Hydrochloride:

10.1 mg of ozanimod hydrochloride was added into a 1.5-mL galss vial followed by adding 0.5 mL of 2-methyltetrahydrofuran to form a suspension. The suspension was stirred at room temperature for 1 week, then white solid was obtained after centrifugation and drying.

Figure 18:
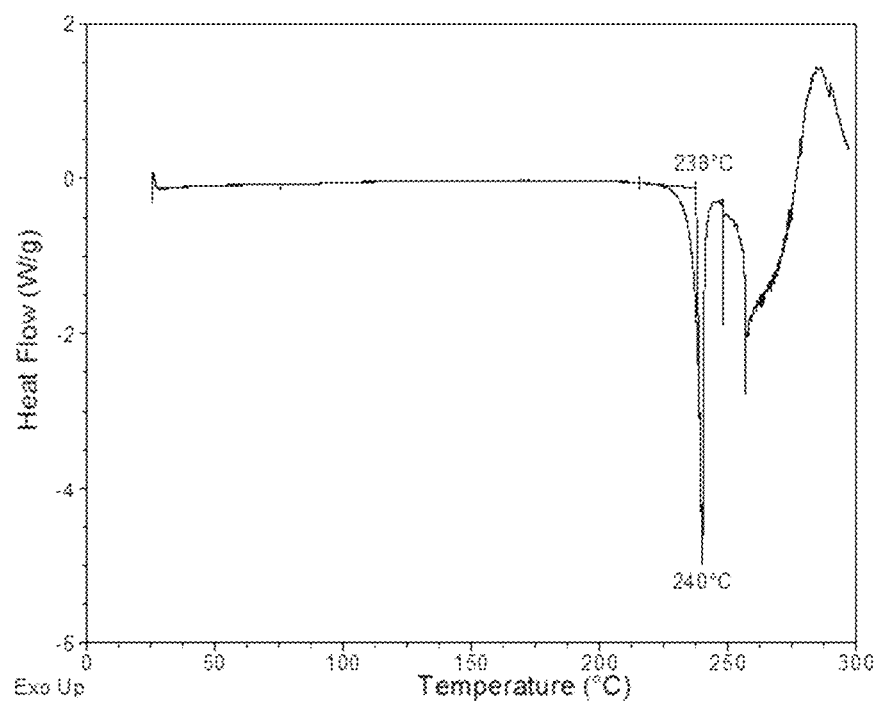
FIG. 18 shows a DSC curve of Form CS1 of hydrochloride obtained in Example 11.
Figure 19:
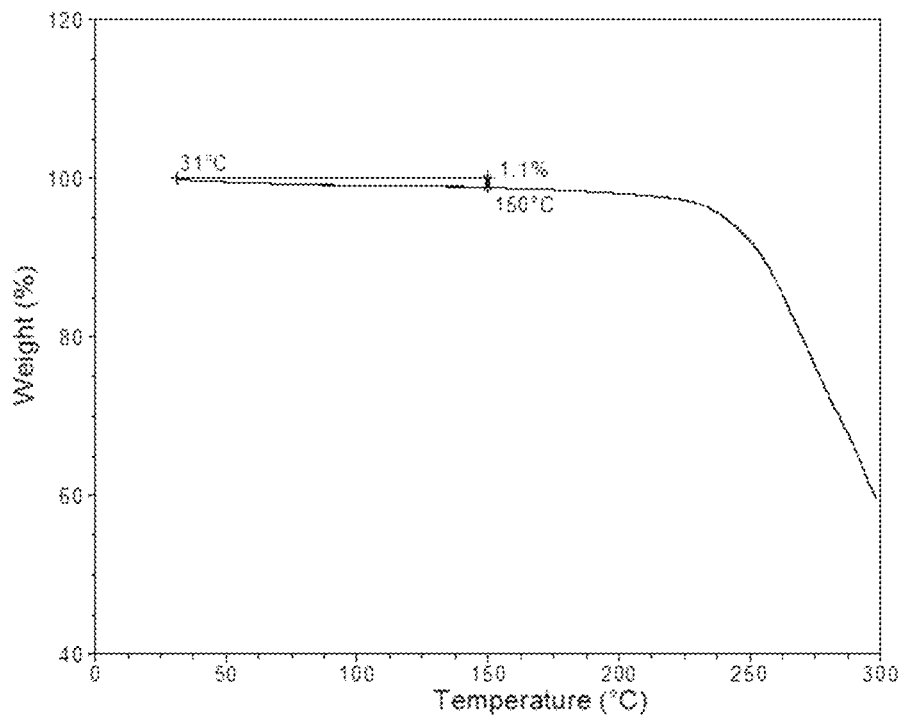
FIG. 19 shows a TGA curve of Form CS1 of hydrochloride obtained in Example 11.
Figure 20:
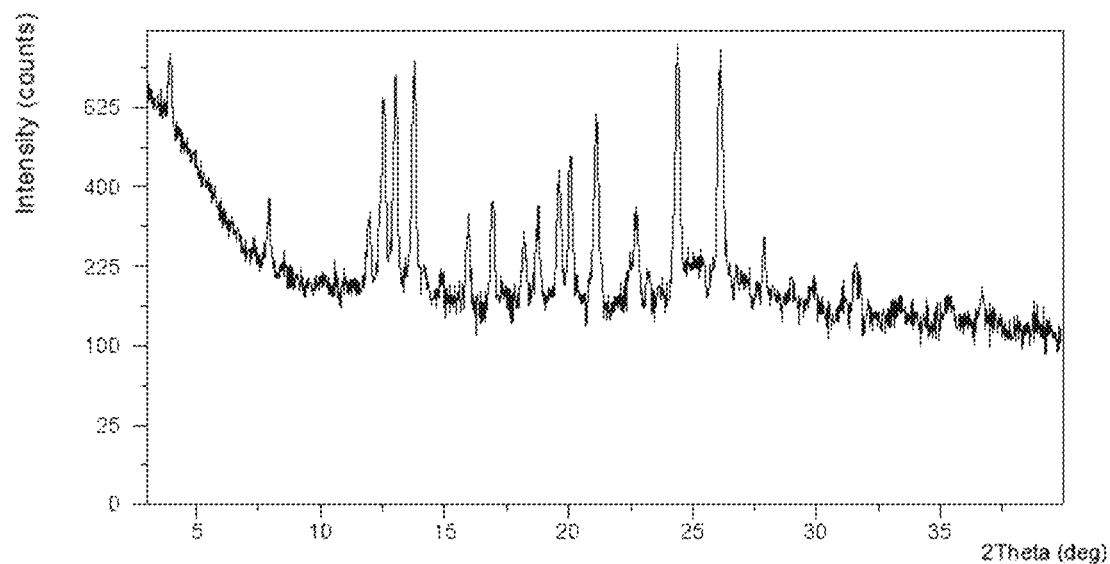
FIG. 20 shows an XRPD pattern of Form CS1 of hydrochloride obtained in Example 11.

The obtained white solid was identified as Form CS1 of ozanimod hydrochloride. The XRPD data of the solid prepared in this example are listed in Table 9. The XRPD pattern is displayed in FIG. 20. The DSC curve is displayed in FIG. 18. The TGA curve is displayed in FIG. 19.

TABLE 9

| 2theta | d spacing | Relatively intensity % |
|---|---|---|
| 3.93 | 22.51 | 58.37 |
| 7.93 | 11.14 | 23.15 |
| 11.95 | 7.41 | 21.69 |
| 12.56 | 7.05 | 70.18 |
| 13.02 | 6.80 | 82.51 |
| 13.77 | 6.43 | 85.16 |
| 14.86 | 5.96 | 6.06 |
| 15.97 | 5.55 | 21.05 |
| 16.91 | 5.24 | 30.15 |
| 18.19 | 4.88 | 20.42 |
| 18.54 | 4.79 | 4.12 |
| 18.79 | 4.72 | 33.76 |
| 19.59 | 4.53 | 38.99 |
| 20.07 | 4.42 | 46.27 |
| 21.11 | 4.21 | 64.20 |
| 22.75 | 3.91 | 26.66 |
| 23.22 | 3.83 | 10.34 |
| 24.41 | 3.65 | 100.00 |
| 26.10 | 3.41 | 93.31 |
| 27.11 | 3.29 | 9.18 |
| 27.90 | 3.20 | 20.23 |
| 28.31 | 3.15 | 6.44 |

TABLE 9-continued

| 2theta | d spacing | Relatively intensity % |
|---|---|---|
| 28.99 | 3.08 | 8.18 |
| 29.85 | 2.99 | 7.60 |
| 31.11 | 2.88 | 5.90 |
| 31.55 | 2.84 | 11.45 |
| 33.37 | 2.69 | 3.80 |
| 35.35 | 2.54 | 5.57 |
| 36.66 | 2.45 | 6.89 |

Example 12

Preparation of Form CS1 of Ozanimod Hydrochloride:

6.0 mg of ozanimod hydrochloride was added into a 1.5-mL galss vial followed by adding 0.5 mL of methanol. The solution was filtered and evaporated quickly at room temperature for 1 week to obtain solid.

Figure 21:
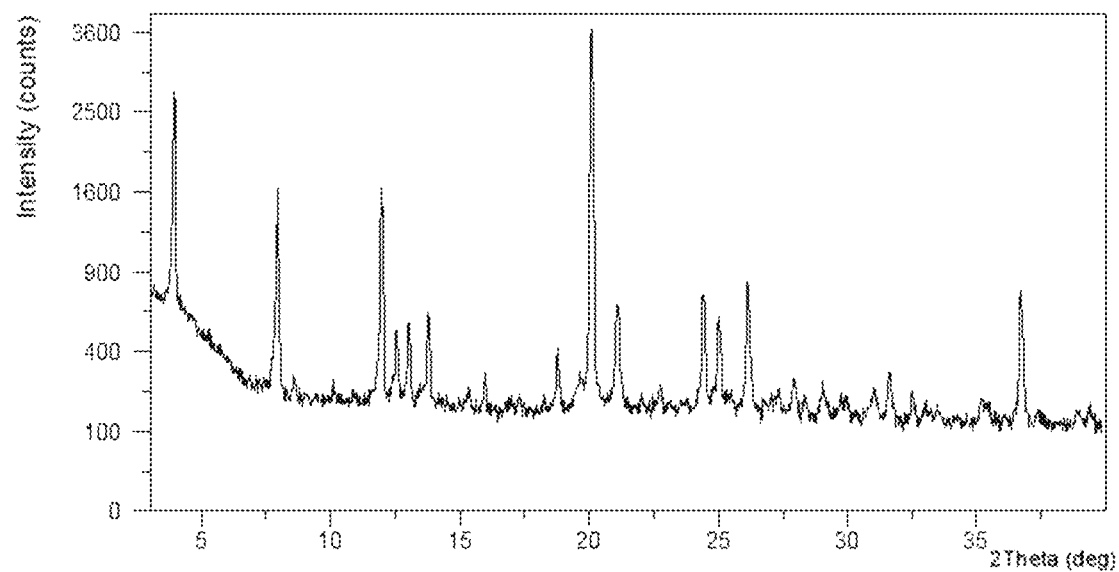
FIG. 21 shows an XRPD pattern of Form CS1 of hydrochloride obtained in Example 12.

The obtained solid was identified as Form CS1 of ozanimod hydrochloride. The XRPD data of the solid prepared in this example are listed in Table 10. The XRPD pattern is displayed in FIG. 21.

TABLE 10

| 2theta | d spacing | Relatively intensity % |
|---|---|---|
| 3.95 | 22.37 | 65.70 |
| 7.94 | 11.13 | 39.57 |
| 8.57 | 10.32 | 2.24 |
| 11.97 | 7.39 | 42.06 |
| 12.55 | 7.05 | 9.32 |
| 13.02 | 6.80 | 10.98 |
| 13.78 | 6.438 | 12.03 |
| 15.33 | 5.78 | 1.81 |
| 15.99 | 5.54 | 3.50 |
| 18.78 | 4.73 | 7.47 |
| 19.61 | 4.53 | 3.45 |
| 20.10 | 4.42 | 100.00 |
| 21.12 | 4.21 | 13.94 |
| 22.73 | 3.91 | 2.92 |
| 24.42 | 3.65 | 17.01 |
| 25.02 | 3.56 | 12.72 |
| 26.14 | 3.41 | 19.94 |
| 27.30 | 3.27 | 2.47 |
| 27.94 | 3.19 | 3.98 |
| 28.34 | 3.15 | 2.68 |
| 29.03 | 3.08 | 2.70 |
| 29.82 | 3.00 | 1.74 |
| 31.03 | 2.88 | 2.53 |
| 31.63 | 2.83 | 5.10 |
| 32.52 | 2.75 | 2.27 |
| 33.49 | 2.68 | 1.55 |
| 35.28 | 2.54 | 1.87 |
| 36.69 | 2.45 | 18.83 |
| 37.44 | 2.40 | 0.94 |
| 38.94 | 2.31 | 1.26 |
| 39.35 | 2.29 | 1.87 |

Example 13

Preparation of Form CS1 of Ozanimod Hydrochloride:

5.5 mg of ozanimod hydrochloride was added into a 1.5-mL galss vial followed by adding 0.8 mL of solvent mixture of methanol and ethyl acetate (3:1, v/v) and 0.2 mg of polymer. The mixture was fast evaporated at room temperature for 1 week to obtain a solid.

Figure 22:
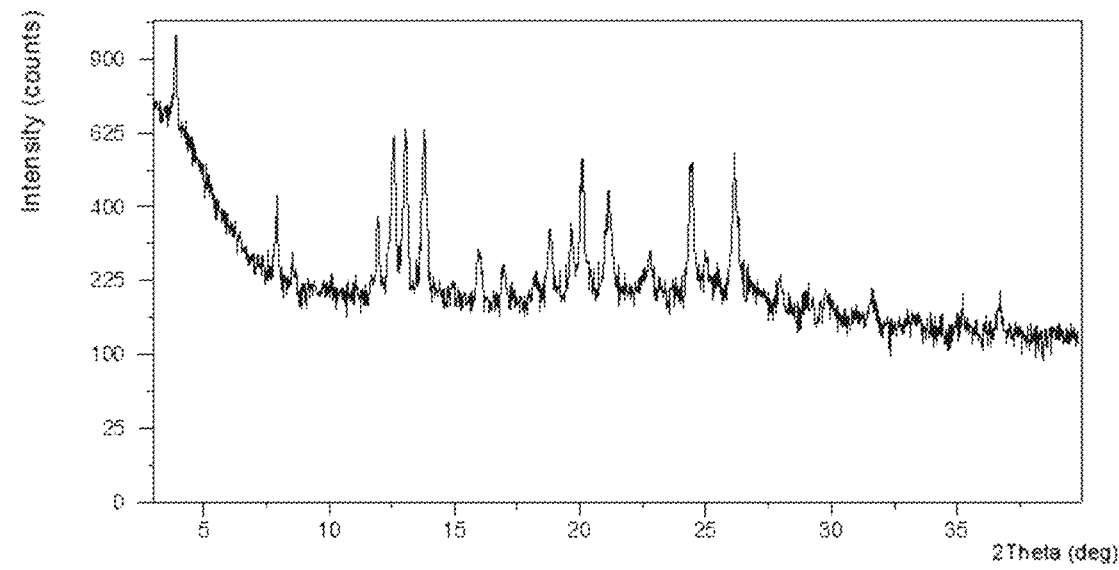
FIG. 22 shows an XRPD pattern of Form CS1 of hydrochloride obtained in Example 13.

The obtained solid was identified as ozanimod hydrochloride Form CS1. The XRPD data of the solid prepared in this example are listed in Table 11. The XRPD pattern is displayed in FIG. 22.

TABLE 11

| 2theta | d spacing | Relatively intensity % |
|---|---|---|
| 3.90 | 22.64 | 100.00 |
| 7.92 | 11.16 | 29.74 |
| 10.98 | 8.06 | 3.07 |
| 11.94 | 7.41 | 33.69 |
| 12.56 | 7.05 | 73.32 |
| 13.05 | 6.78 | 78.29 |
| 13.78 | 6.43 | 78.88 |
| 14.94 | 5.93 | 6.31 |
| 16.04 | 5.52 | 17.30 |
| 16.96 | 5.23 | 14.47 |
| 18.21 | 4.87 | 11.10 |
| 18.76 | 4.73 | 29.38 |
| 19.63 | 4.53 | 30.08 |
| 20.09 | 4.42 | 62.83 |
| 21.13 | 4.20 | 51.45 |
| 22.74 | 3.91 | 20.95 |
| 24.42 | 3.65 | 70.20 |
| 24.99 | 3.56 | 20.32 |
| 26.12 | 3.41 | 67.91 |
| 27.99 | 3.19 | 13.24 |
| 29.06 | 3.07 | 8.71 |
| 29.82 | 3.00 | 10.52 |
| 31.67 | 2.83 | 11.02 |
| 35.31 | 2.54 | 3.40 |
| 36.72 | 2.45 | 9.56 |
| 39.04 | 2.31 | 1.86 |

Example 14

Preparation of Form CS1 of Ozanimod Hydrochloride:

5.9 mg of ozanimod hydrochloride solid was added into a 1.5-mL glass vial followed by adding 0.3 mL of dimethylacetamide. The clear solution was placed into a 20-mL glass vial containing 5 mL of tetrahydrofuran for liquid vapor diffusion for 1 week. Then the obtained suspension was filtered and dried to obtain white solid.

Figure 23:
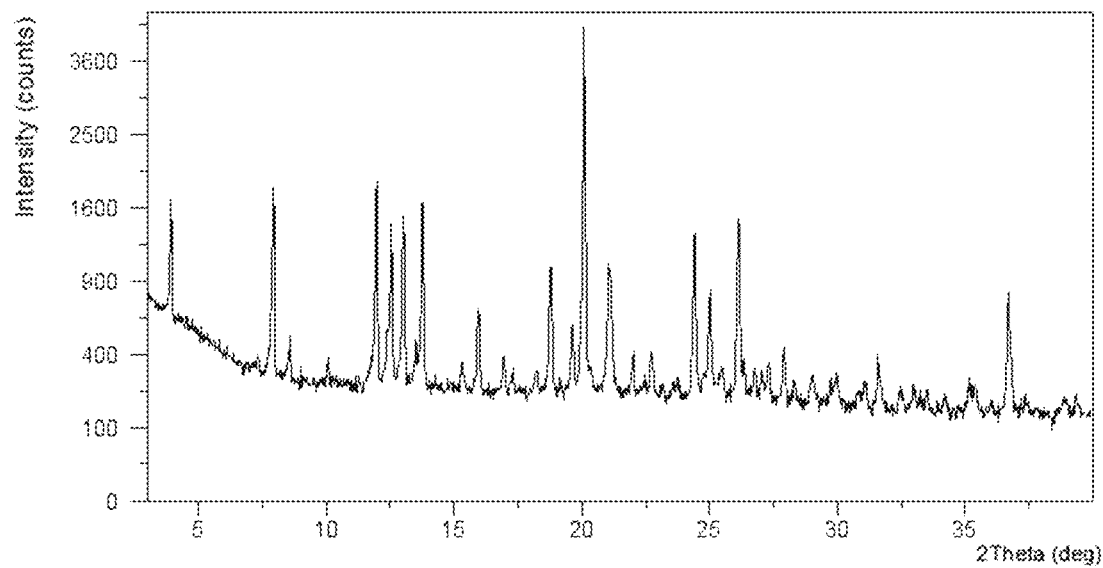
FIG. 23 shows an XRPD pattern of Form CS1 of hydrochloride obtained in Example 14.

The obtained white solid was identified as ozanimod hydrochloride Form CS1. The XRPD data of the solid prepared in this example are listed in Table 12. The XRPD pattern is displayed in FIG. 23.

TABLE 12

| 2theta | d spacing | Relatively intensity % |
|---|---|---|
| 3.94 | 22.42 | 29.02 |
| 7.94 | 11.13 | 40.24 |
| 8.59 | 10.30 | 6.70 |
| 10.08 | 8.78 | 3.14 |
| 11.98 | 7.39 | 43.32 |
| 12.56 | 7.05 | 30.75 |
| 13.03 | 6.79 | 34.04 |
| 13.78 | 6.42 | 38.84 |
| 15.31 | 5.79 | 2.91 |
| 15.96 | 5.55 | 12.46 |
| 16.95 | 5.23 | 4.31 |
| 17.31 | 5.12 | 2.90 |
| 18.22 | 4.87 | 2.15 |
| 18.79 | 4.72 | 20.42 |
| 19.62 | 4.52 | 8.57 |
| 20.10 | 4.42 | 100.00 |
| 21.08 | 4.22 | 21.17 |
| 22.03 | 4.04 | 4.56 |
| 22.73 | 3.91 | 5.82 |
| 24.40 | 3.65 | 30.21 |
| 25.01 | 3.56 | 16.38 |
| 25.47 | 3.50 | 3.80 |
| 26.13 | 3.41 | 34.94 |
| 26.77 | 3.33 | 4.27 |
| 27.02 | 3.30 | 3.66 |
| 27.30 | 3.27 | 5.18 |
| 27.90 | 3.20 | 6.81 |
| 29.01 | 3.08 | 2.92 |
| 29.98 | 2.98 | 3.94 |
| 31.07 | 2.88 | 2.48 |
| 31.57 | 2.83 | 6.30 |
| 32.48 | 2.76 | 2.04 |
| 32.96 | 2.72 | 2.06 |
| 34.21 | 2.62 | 1.44 |
| 35.27 | 2.54 | 2.38 |
| 36.68 | 2.45 | 17.57 |
| 38.85 | 2.32 | 2.01 |

Example 15

Preparation of Form CS1 of Ozanimod Hydrochloride:

5.4 mg of ozanimod hydrochloride was added into a 1.5-mL galss vial followed by adding 0.3 mL of solvent mixture of methanol and water (9:1, v/v) at 50° C. The mixture was filtered and fast cooled at −20° C. to obtain solid.

Figure 24:
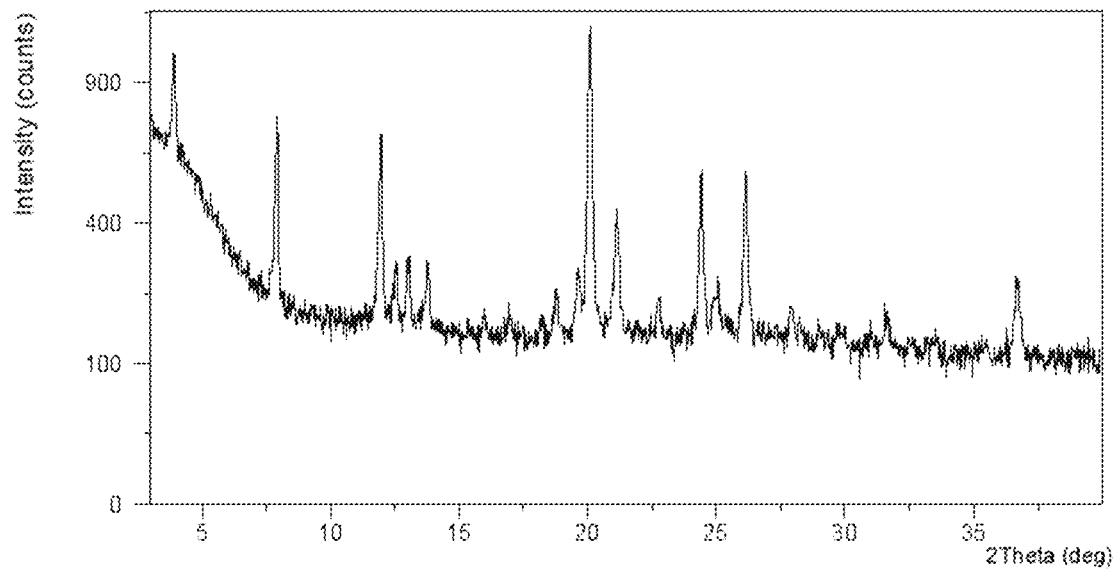
FIG. 24 shows an XRPD pattern of Form CS1 of hydrochloride obtained in Example 15.

The obtained white solid was identified as Form CS1 of ozanimod hydrochloride. The XRPD data of the solid prepared in this example are listed in Table 13. The XRPD pattern is displayed in FIG. 24.

TABLE 13

| 2theta | d spacing | Relatively intensity % |
|---|---|---|
| 3.92 | 22.54 | 56.68 |
| 7.94 | 11.14 | 51.15 |
| 9.36 | 9.45 | 1.72 |
| 9.89 | 8.95 | 3.02 |
| 11.96 | 7.40 | 51.80 |
| 12.57 | 7.04 | 11.98 |
| 13.04 | 6.79 | 15.16 |
| 13.79 | 6.42 | 12.00 |
| 15.96 | 5.55 | 3.10 |
| 16.95 | 5.23 | 3.28 |
| 18.21 | 4.87 | 4.07 |
| 18.78 | 4.73 | 9.66 |
| 19.69 | 4.51 | 12.34 |
| 20.08 | 4.42 | 100.00 |
| 21.11 | 4.21 | 27.35 |
| 21.87 | 4.06 | 5.55 |
| 22.77 | 3.91 | 7.92 |
| 24.40 | 3.65 | 44.75 |
| 25.00 | 3.56 | 10.24 |
| 26.13 | 3.41 | 43.35 |
| 26.80 | 3.33 | 6.64 |
| 27.91 | 3.20 | 6.55 |
| 28.96 | 3.08 | 3.94 |
| 29.86 | 2.99 | 2.81 |
| 31.57 | 2.83 | 7.26 |
| 33.39 | 2.68 | 2.12 |
| 36.71 | 2.45 | 15.24 |

Example 16

Figure 25:
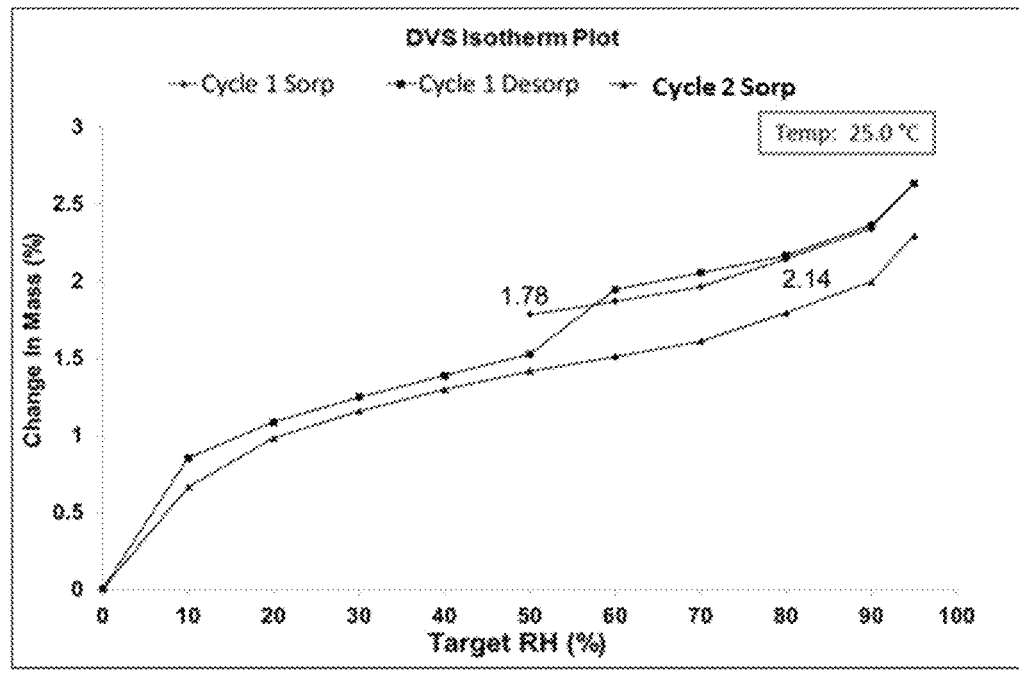
FIG. 25 shows a DVS plot of Form CS1 in Example 16.

Hygroscopicity Assessment of Form CS1 of Ozanimod:

Dynamic vapor sorption (DVS) was applied to test hygroscopicity of Form CS1 with about 10 mg of samples. The result is listed in Table 14. The DVS plot is shown in FIG. 25.

TABLE 14

| Crystal Form | Weight gain under 80% RH |
|---|---|
| Form CS1 | 0.36% |

The results indicates that the weight gain of Form CS1 under 80% RH is 0.36%. According to the definition of hygroscopicity, Form CS1 belongs to slightly hygroscopic.

Example 17

Figure 26:
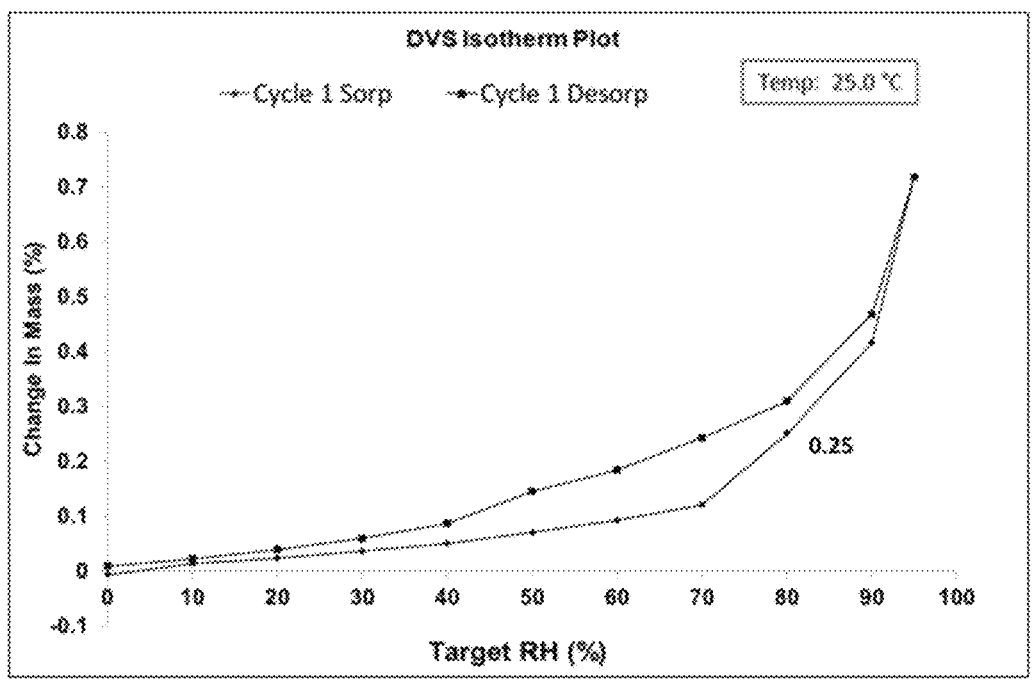
FIG. 26 shows a DVS plot of Form CS2 in Example 17.

Hygroscopicity Assessment of Form CS2 of Ozanimod:

Dynamic vapor sorption (DVS) was applied to test hygroscopicity of Form CS2 with about 10 mg of samples. The result is listed in Table 15. The DVS plot is shown in FIG. 26.

TABLE 15

| Crystal Form | Weight gain under 80% RH |
|---|---|
| Form CS2 | 0.25% |

The results indicates that the weight gain of Form CS2 under 80% RH is 0.25%. According to the definition of hygroscopicity, Form CS2 belongs to slightly hygroscopic.

Example 18

Figure 27:
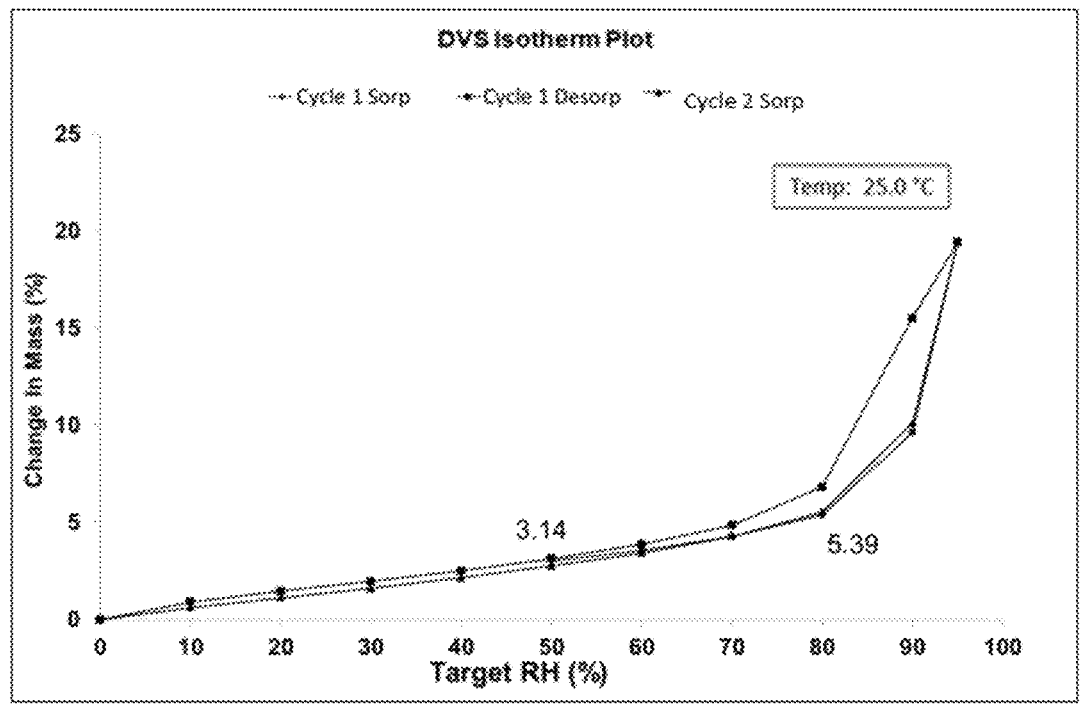
FIG. 27 shows a DVS plot of Form CS3 in Example 18.

Hygroscopicity Assessment of Form CS3 of Ozanimod:

Dynamic vapor sorption (DVS) was applied to test hygroscopicity of Form CS3 with about 10 mg of samples. The result is listed in Table 16. The DVS plot is shown in FIG. 27.

TABLE 16

| Crystal Form | Weight gain under 80% RH |
|---|---|
| Form CS3 | 2.25% |

The results indicates that the weight gain of Form CS3 under 80% RH is 2.25%.

Example 19

Figure 28:
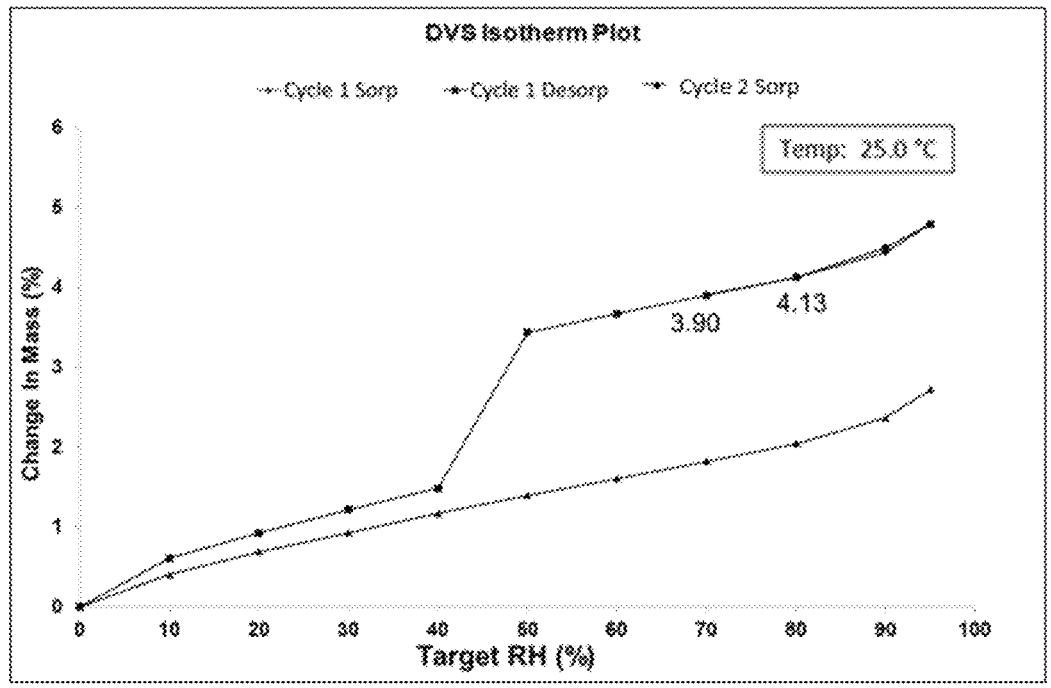
FIG. 28 shows a DVS plot of Form CS5 in Example 19.

Hygroscopicity Assessment of Form CS5 of Ozanimod:

Dynamic vapor sorption (DVS) was applied to test hygroscopicity of Form CS5 with about 10 mg of samples. The result is listed in Table 17. The DVS plot is shown in FIG. 28.

TABLE 17

| Crystal Form | Weight gain under 80% RH |
|---|---|
| Form CS5 | 0.23% |

The results indicates that the weight gain of Form CS5 under 80% RH is 0.23%. According to the definition of hygroscopicity, Form CS5 belongs to slightly hygroscopic.

Example 20

Figure 29:
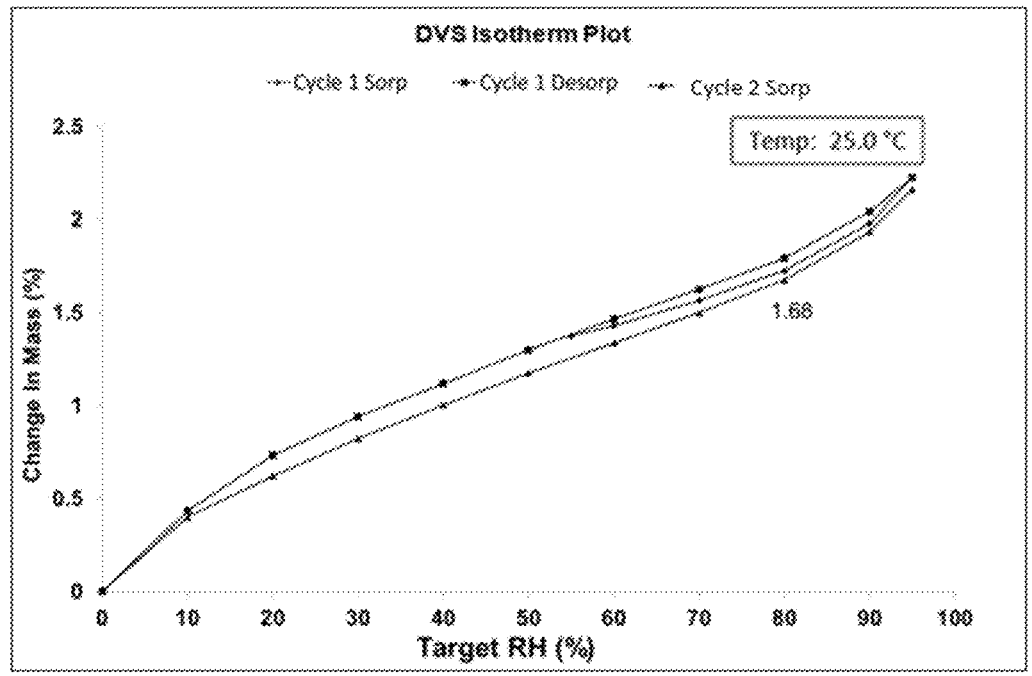
FIG. 29 shows a DVS plot of Form CS6 in Example 20.

Hygroscopicity Assessment of Form CS6 of Ozanimod:

Dynamic vapor sorption (DVS) was applied to test hygroscopicity of Form CS6 with about 10 mg of samples. The result is listed in Table 18. The DVS plot is shown in FIG. 29.

TABLE 18

| Crystal Form | Weight gain under 80% Relative Humidity |
|---|---|
| Form CS6 | 1.68% |

The results indicates that the weight gain of Form CS6 under 80% RH is 1.68%.

Example 21

Figure 30:
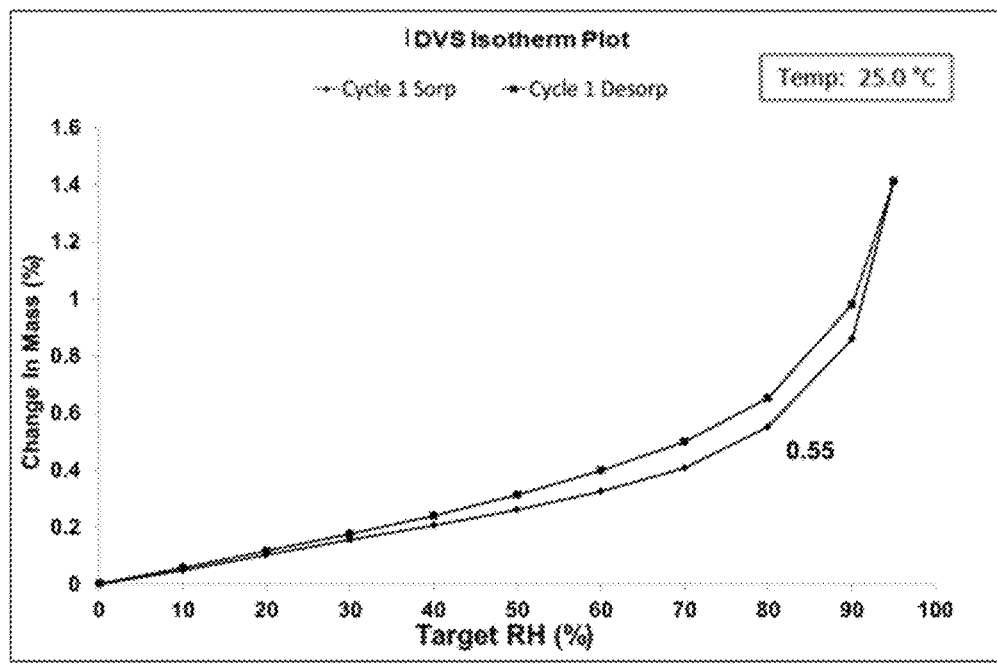
FIG. 30 shows a DVS plot of Form CS1 of hydrochloride in Example 21.

Hygroscopicity Assessment of Form CS1 of Ozanimod Hydrochloride:

Dynamic vapor sorption (DVS) was applied to test hygroscopicity of Form CS1 of ozanimod hydrochloride with about 10 mg of samples. The result is listed in Table 19. The DVS plot is shown in FIG. 30.

TABLE 19

| Crystal Form | Weight gain under 80% Relative Humidity |
|---|---|
| ozanimod hydrochloride Form CS1 | 0.55% |

The results indicates that the weight gain of Form CS1 of ozanimod hydrochloride under 80% RH is 0.55%. According to the definition standard of hygroscopicity, ozanimod hydrochloride Form CS1 was slightly hygroscopic.

Description and definition of hygroscopicity (Chinese Pharmacopoeia 2015 edition appendix Drug hygroscopic test guidelines, test at 25° C.+/−1° C., 80% RH).

deliquescent: Sufficient water is absorbed to form a liquid;
very hygroscopic: Increase in mass is equal to or greater than 15 percent;
hygroscopic: Increase in mass is less than 15 percent and equal to or greater than 2 percent;
slightly hygroscopic: Increase in mass is less than 2 percent and equal to or greater than 0.2 percent.
non hygroscopic or almost non hygroscopic: Increase in mass is less than 0.2 percent.

Example 22

Figure 31:
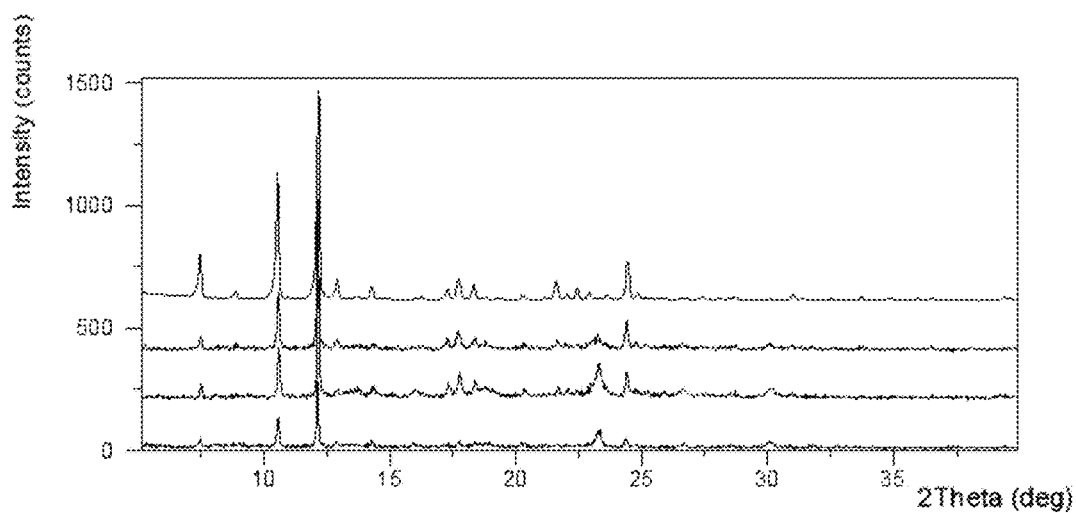
FIG. 31 shows an XRPD comparison pattern of Form CS1 before and after stability test in Example 22.

Stability Assessment of Form CS1 of Ozanimod:

Three solid samples of Form CS1 were placed in constant temperature and humidity chambers at 25° C./60% RH, 40° C./75% RH and 60° C./75% RH for 4 weeks. XRPD was used to test the crystalline form at the end of week 4. HPLC was used to measure the chemical purity at the end of week 1, 2, and 4. The XRPD comparison result is shown in FIG. 31 (from top to bottom: XRPD pattern of Form CS1 before and after being stored under 25° C./60% RH, 40° C./75% RH and 60° C./75% RH for 4 weeks), and the results are shown in Table 20.

TABLE 20

| Initial Form | Conditions | 1 week purity % | 2 week purity % | 4 week purity % | Change of the crystalline form |
|---|---|---|---|---|---|
| Form CS1 | 25° C./60% RH | 99.12 | 99.18 | 98.97 | No change |
| Form CS1 | 40° C./75% RH | 99.16 | 99.17 | 98.92 | No change |
| Form CS1 | 60° C./75% RH | 99.26 | 99.13 | 98.71 | No change |

No form change and obvious purity decrease were observed for Form CS1 after being stored at 25° C./60% RH, 40° C./75% RH and 60° C./75% RH for 4 weeks. The result shows that Form CS1 has good stability.

Example 23

Figure 32:
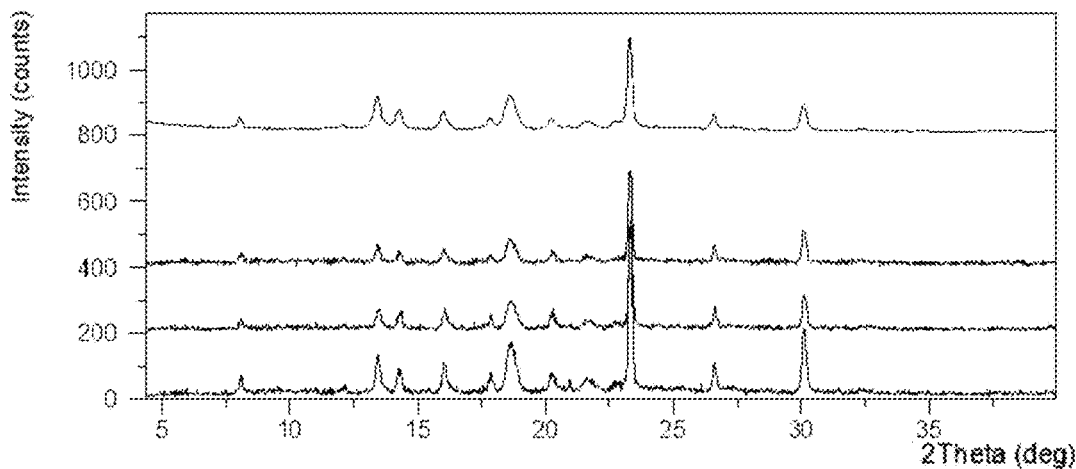
FIG. 32 shows an XRPD comparison pattern of Form CS2 before and after stability test in Example 23.

Stability Assessment of Form CS2 of Ozanimod:

Four solid samples of Form CS2 were placed in constant temperature and humidity chambers at 25° C./60% RH, 40° C./75% RH and 60° C./75% RH for 4 weeks and 80° C. for 1 week. XRPD was used to test the crystalline form at the end of week 4. HPLC was used to measure the chemical purity at the end of week 1, 2, and 4. The XRPD comparison result is shown in FIG. 32 (from top to bottom: XRPD pattern of Form CS2 before and after being stored under 25° C./60% RH, 40° C./75% RH and 60° C./75% RH for 4 weeks and 80° C. for 1 week), and the results are shown in Table 21.

TABLE 21

| Initial Form | Conditions | 1 week purity % | 2 week purity % | 4 week purity % | Change of the crystalline form |
|---|---|---|---|---|---|
| Form CS2 | 25° C./60% RH | 99.85 | 99.63 | 99.62 | No change |
| Form CS2 | 40° C./75% RH | 99.84 | 99.78 | 99.55 | No change |
| Form CS2 | 60° C./75% RH | 99.91 | 99.60 | 99.63 | No change |
| Form CS2 | 80° C. | 99.71 | N/A | N/A | No change |

N/A indicates not tested in this embodiment.

No form change and obvious purity decrease were observed for Form CS2 after being stored at 25° C./60% RH, 40° C./75% RH and 60° C./75% RH for 4 weeks and 80° C. for 1 week. It can be seen that Form CS2 has good stability.

Example 24

Figure 33:
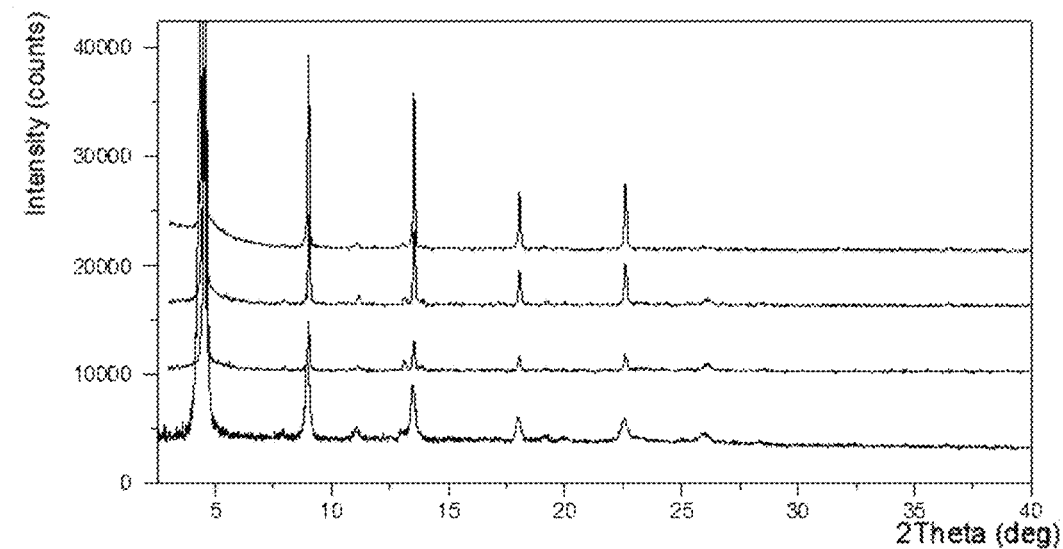
FIG. 33 shows an XRPD comparison pattern of Form CS3 before and after stability test in Example 24.

Stability Assessment of Form CS3 of Ozanimod:

Three solid samples of Form CS3 were placed in constant temperature and humidity chambers at 25° C./60% RH, 40° C./75% RH and 60° C./75% RH for 4 weeks. XRPD was used to test the crystalline form at the end of week 4. HPLC was used to measure the chemical purity at the end of week 1, 2, and 4. The XRPD comparison pattern is shown in FIG. 33 (from top to bottom: XRPD pattern of Form CS3 before and after being stored under 25° C./60% RH, 40° C./75% RH and 60° C./75% RH for 4 weeks), and the results are shown in Table 22.

TABLE 22

| Initial Form | Conditions | 1 week purity % | 2 week purity % | 4 week purity % | Change of the crystalline form |
|---|---|---|---|---|---|
| Form CS3 | 25° C./60% RH | 99.53 | 99.30 | 99.31 | No change |
| Form CS3 | 40° C./75% RH | 99.52 | 99.28 | 99.17 | No change |
| Form CS3 | 60° C./75% RH | 99.36 | 98.84 | 98.54 | No change |

No form change and obvious purity decrease were observed for Form CS3 after being stored at 25° C./60% RH, 40° C./75% RH and 60° C./75% RH for 4 weeks. It can be seen that Form CS3 has good stability.

Example 25

Figure 34:
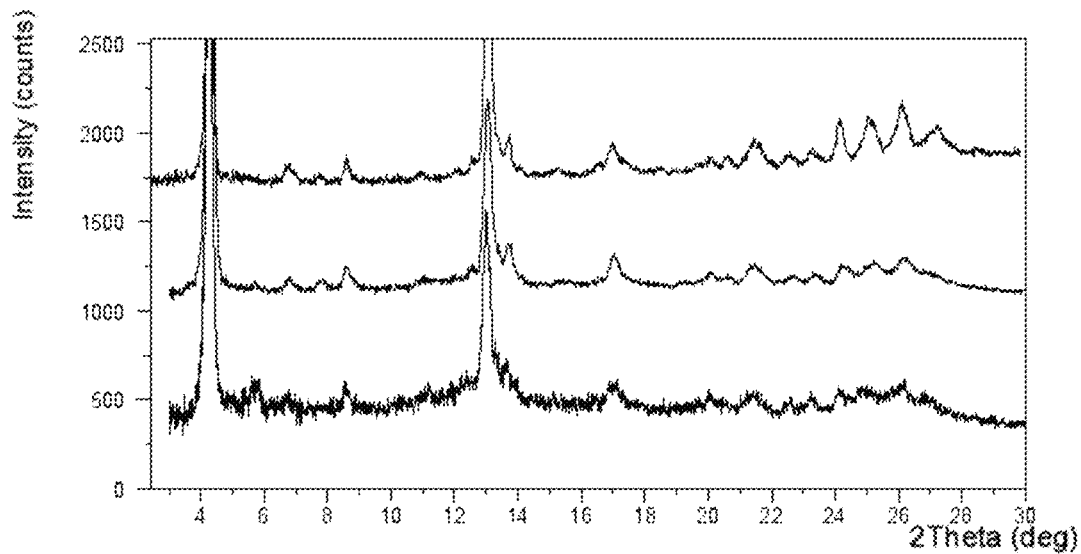
FIG. 34 shows an XRPD comparison pattern of Form CS5 before and after stability test in Example 25.

Stability Assessment of Form CS5 of Ozanimod:

Three solid samples of Form CS5 were placed in constant temperature and humidity chambers at 25° C./60% RH, 40° C./75% RH and 60° C./75% RH for 2 weeks. XRPD was used to test the crystalline form at the end of week 4. The XRPD comparison pattern is shown in FIG. 34 (from top to bottom: XRPD pattern of Form CS5 before and after being stored under 25° C./60% RH, 40° C./75% RH and 60° C./75% RH for 2 weeks), and the results are shown in Table 23.

TABLE 23

| Initial Form | Conditions | Time | Change of the crystalline form |
|---|---|---|---|
| Form CS5 | 25° C./60% RH | 2 weeks | No change |
| Form CS5 | 40° C./75% RH | 2 weeks | No change |
| Form CS5 | 60° C./75% RH | 2 weeks | No change |

No form change and obvious purity decrease was observed for Form CS5 after being stored at 25° C./60% RH, 40° C./75% RH and 60° C./75% RH for 2 weeks. It can be seen that Form CS5 has good stability.

Example 26

Figure 35:
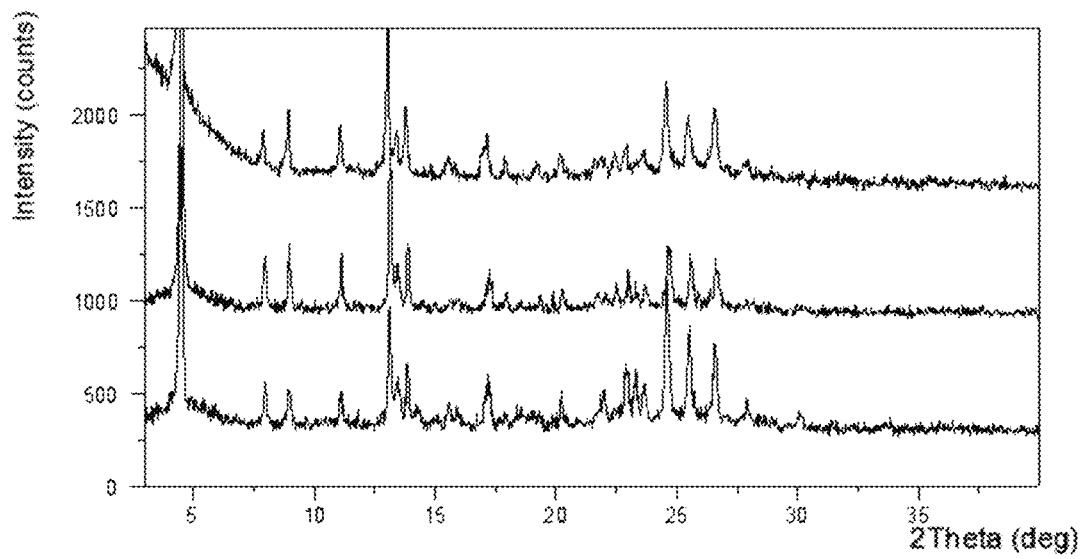
FIG. 35 shows an XRPD comparison pattern of Form CS6 before and after stability test in Example 26.

Stability Assessment of Form CS6 of Ozanimod:

Two samples of Form CS6 were placed in constant temperature and humidity chambers at 25° C./60% RH and 40° C./75% RH for 4 weeks. XRPD was used to test the crystalline form at the end of week 4. HPLC was used to measure the chemical purity at the end of week 1, 2, and 4. The XRPD comparison result is shown in FIG. 35 (from top to bottom: XRPD pattern of Form CS6 before and after being stored under 25° C./60% RH and 40° C./75% RH for 4 weeks), and the results are shown in Table 24.

TABLE 24

| Initial Form | Conditions | 1 week purity % | 2 week purity % | 4 week purity % | Change of the crystalline form |
|---|---|---|---|---|---|
| Form CS6 | 25° C./60% RH | 98.44 | 98.21 | 98.27 | No change |
| Form CS6 | 40° C./75% RH | 98.47 | 98.33 | 97.97 | No change |

No form change and obvious purity decrease were observed for Form CS6 after being stored at 25° C./60% RH and 40° C./75% RH for 4 weeks. It can be seen that Form CS6 has good stability.

Example 27

Figure 36:
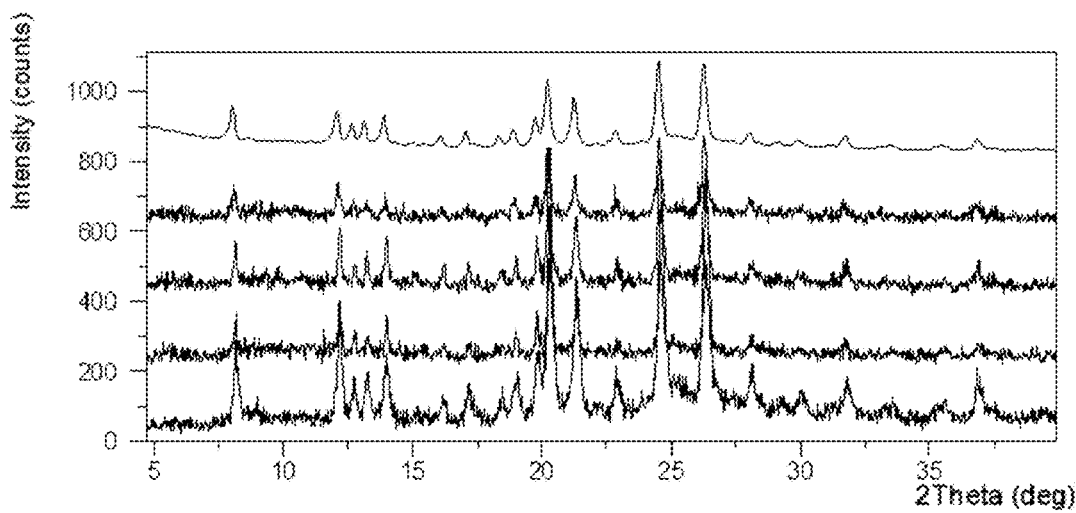
FIG. 36 shows an XRPD comparison pattern of Form CS1 of hydrochloride before and after stability test in Example 27.

Stability Assessment of Form CS1 of Ozanimod Hydrochloride:

Four samples of Form CS1 of ozanimod hydrochloride were placed in constant temperature and humidity chambers at 25° C./60% RH, 40° C./75% RH and 60° C./75% RH for 4 weeks and 80° C. for 1 week. XRPD was used to test the crystalline form at the end of week 4. HPLC was used to measure the chemical purity at the end of week 1, 2, and 4. The XRPD comparison pattern is shown in FIG. 36 (from top to bottom: XRPD pattern of ozanimod hydrochloride Form CS1 before and after being stored under 25° C./60% RH, 40° C./75% RH and 60° C./75% RH for 4 weeks and 80° C. for 1 week), and the results are shown in Table 25.

TABLE 25

| Initial Form | Conditions | 1 week purity % | 2 week purity % | 4 week purity % | Change of the crystalline form |
|---|---|---|---|---|---|
| Form CS1 of ozanimod hydrochloride | 25° C./60% RH | 99.18 | 99.13 | 99.22 | No change |
| Form CS1 of ozanimod hydrochloride | 40° C./75% RH | 99.15 | 99.12 | 99.24 | No change |
| Form CS1 of ozanimod hydrochloride | 60° C./75% RH | 99.25 | 99.25 | 99.36 | No change |
| Form CS1 of ozanimod hydrochloride | 80° C. | 99.34 | N/A | N/A | No change |

No form change and obvious purity decrease were observed for ozanimod hydrochloride Form CS1 after being stored at 25° C./60% RH, 40° C./75% RH and 60° C./75% RH for 4 weeks and 80° C. for 1 week. It can be seen that Form CS1 of ozanimod hydrochloride has good stability.

Example 28

Particle size distribution:

Certain amount of samples of Form CS1, Form CS2, Form CS3, Form CS5, Form CS6 of ozanimod and Form CS1 of ozanimod hydrochloride were taken for particle size distribution test. The results are shown in Table 26.

TABLE 26

| Form | MV (μm) | SD (μm) | D10 (μm) | D50 (μm) | D90 (μm) |
|---|---|---|---|---|---|
| Form CS1 | 22.40 | 15.08 | 3.15 | 11.20 | 48.90 |
| Form CS2 | 23.24 | 11.21 | 5.78 | 14.20 | 42.35 |
| Form CS3 | 66.62 | 39.31 | 20.36 | 51.80 | 130.8 |
| Form CS5 | 68.84 | 61.69 | 6.55 | 41.10 | 173.3 |
| Form CS6 | 68.91 | 54.79 | 12.87 | 46.47 | 161.7 |
| Form CS1 of ozanimod hydrochloride | 200.7 | 168.4 | 20.84 | 180.8 | 397.7 |

Mv: Average particle size calculated by volume.
SD: Standard deviation
D10: particle size which accounts for 10% of the particle size distribution (volume distribution).
D50: particle size which accounts for 50% of the particle size distribution (volume distribution), also known as the median diameter.
D90: particle size which accounts for 90% of the particle size distribution (volume distribution).

Figure 37:
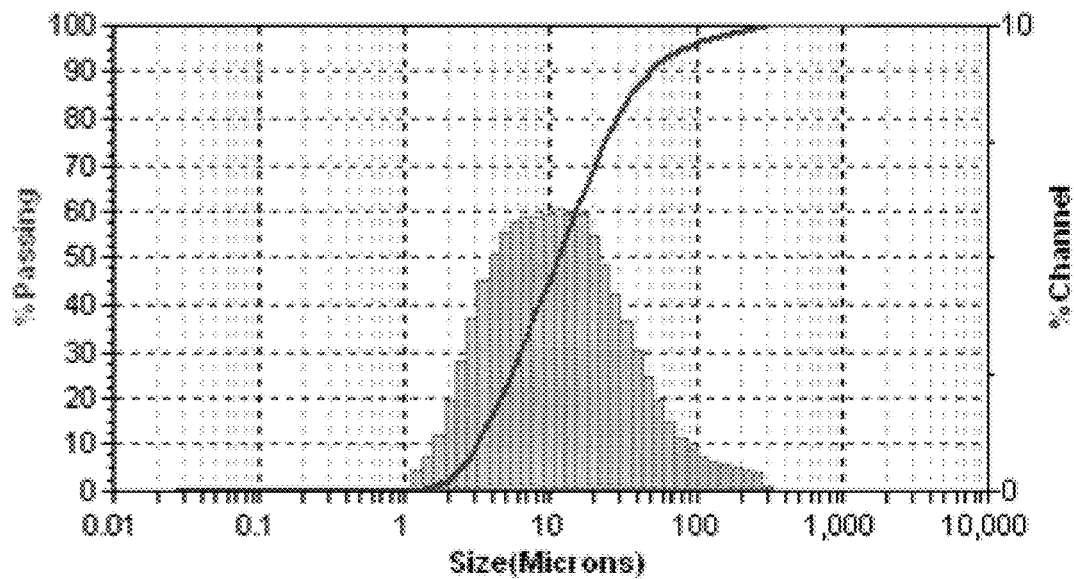
FIG. 37 shows a PSD diagram of Form CS1 in Example 28.

The particle size distribution diagram of Form CS1 is shown in FIG. 37. The result shows that the average particle size of Form CS1 is 22.40 μm, and the particle size distribution is narrow, which presents an almost normal and uniform distribution.

Figure 38:
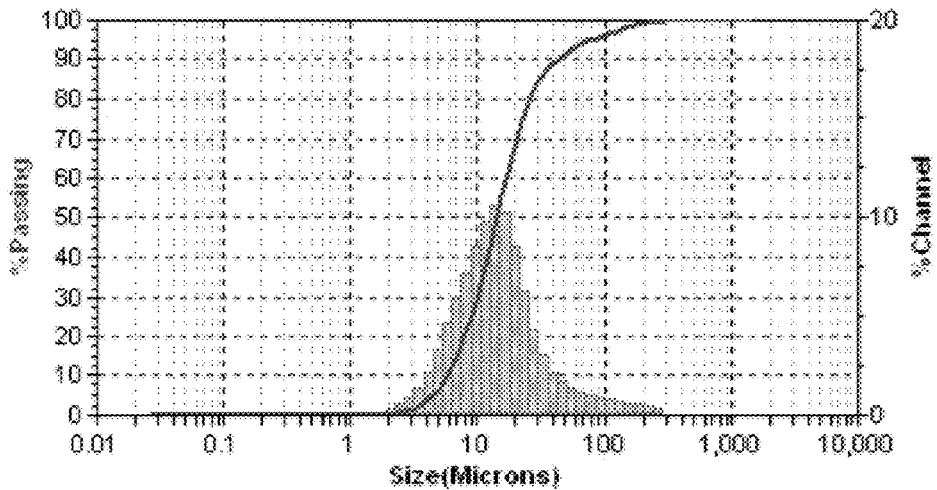
FIG. 38 shows a PSD diagram of Form CS2 in Example 28.

The particle size distribution diagram of Form CS2 is shown in FIG. 38. The result shows that the average particle size of Form CS2 is 23.24 μm, and the particle size distribution is narrow, which presents an almost normal and uniform distribution.

Figure 39:
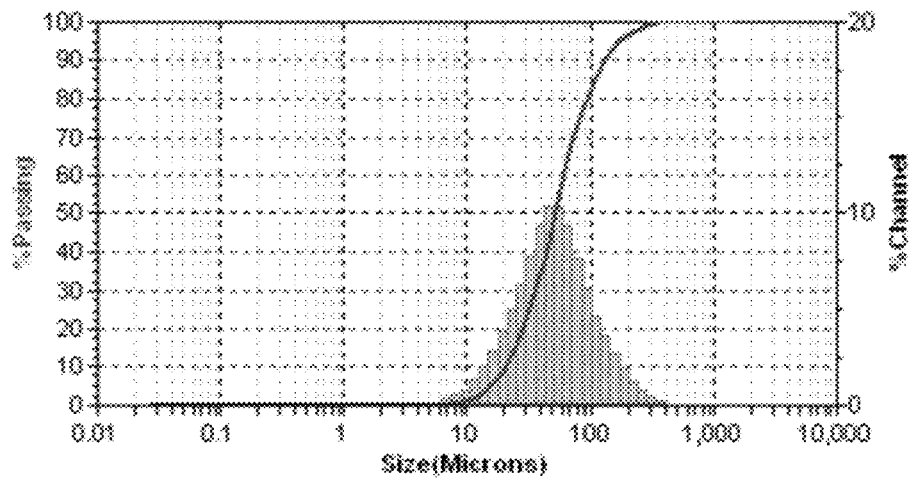
FIG. 39 shows a PSD diagram of Form CS3 in Example 28.

The particle size distribution diagram of Form CS3 is shown in FIG. 39. The result shows that the average particle size of Form CS3 is 66.62 μm, and the particle size distribution is narrow, which presents an almost normal and uniform distribution.

Figure 40:
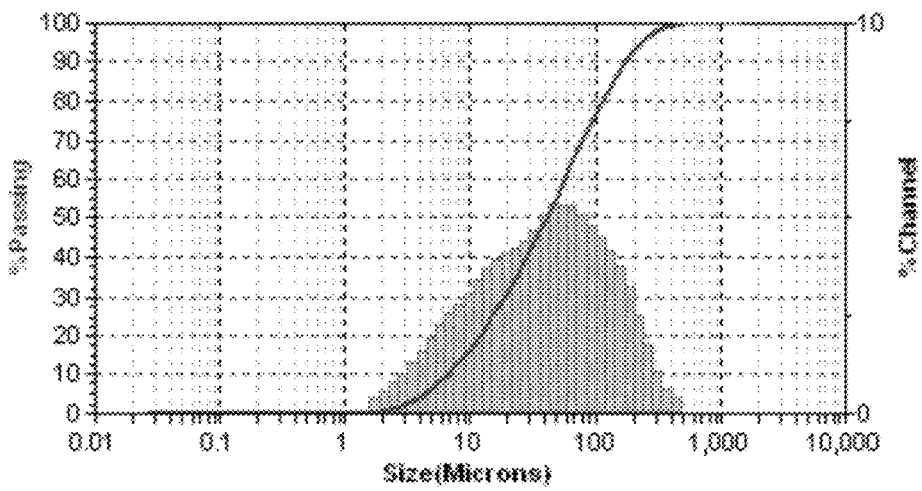
FIG. 40 shows a PSD diagram of Form CS5 in Example 28.

The particle size distribution diagram of Form CS5 is shown in FIG. 40. The result shows that the average particle size of Form CS5 is 68.84 μm, and the particle size distribution is narrow, which presents an almost normal and uniform distribution.

Figure 41:
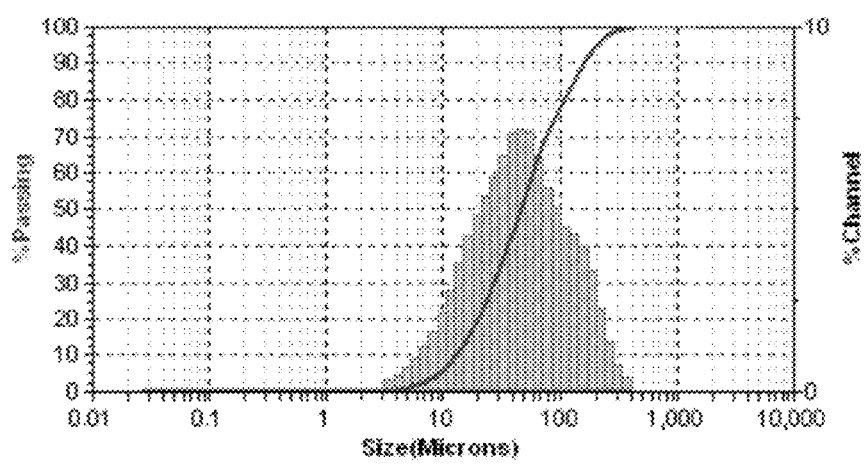
FIG. 41 shows a PSD diagram of Form CS6 in Example 28.

The particle size distribution diagram of Form CS6 is shown in FIG. 41. The result shows that the average particle size of Form CS6 is 68.91 μm, and the particle size distribution is narrow, which presents an almost normal and uniform distribution.

Figure 42:
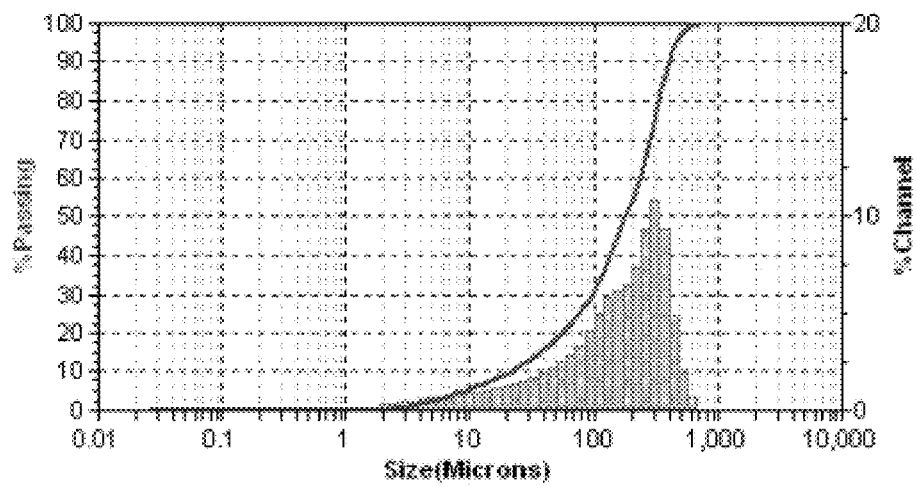
FIG. 42 shows a PSD diagram of Form CS1 of hydrochloride in Example 28.
Figure 43:
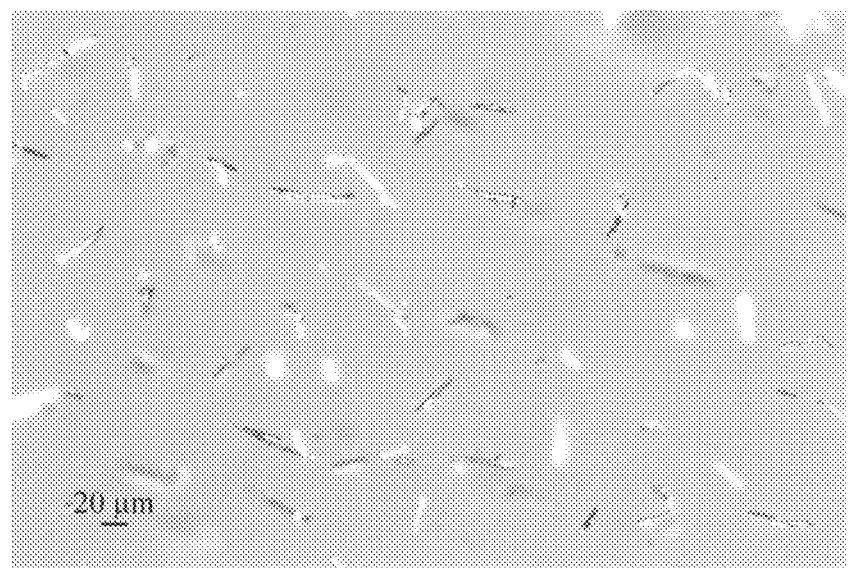
FIG. 43 shows a PLM image of Form CS1 in Example 28.
Figure 44:
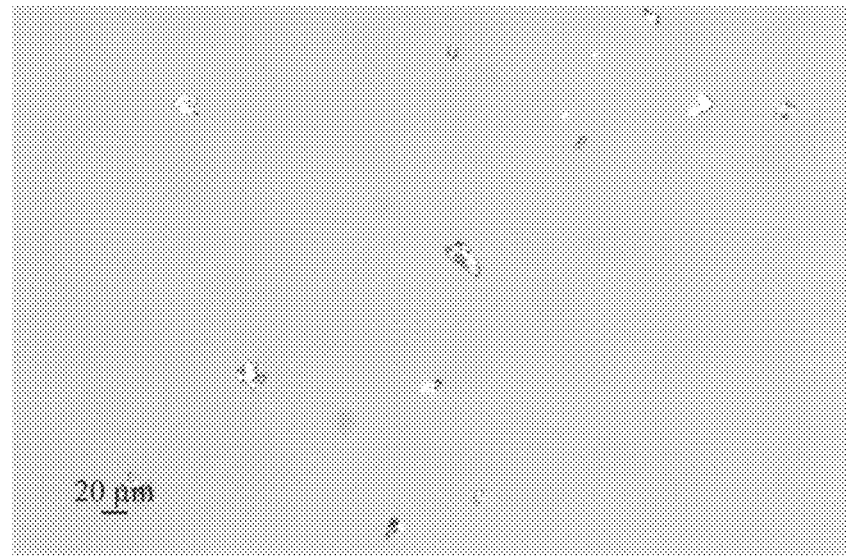
FIG. 44 shows a PLM image of Form CS2 in Example 28.
Figure 45:
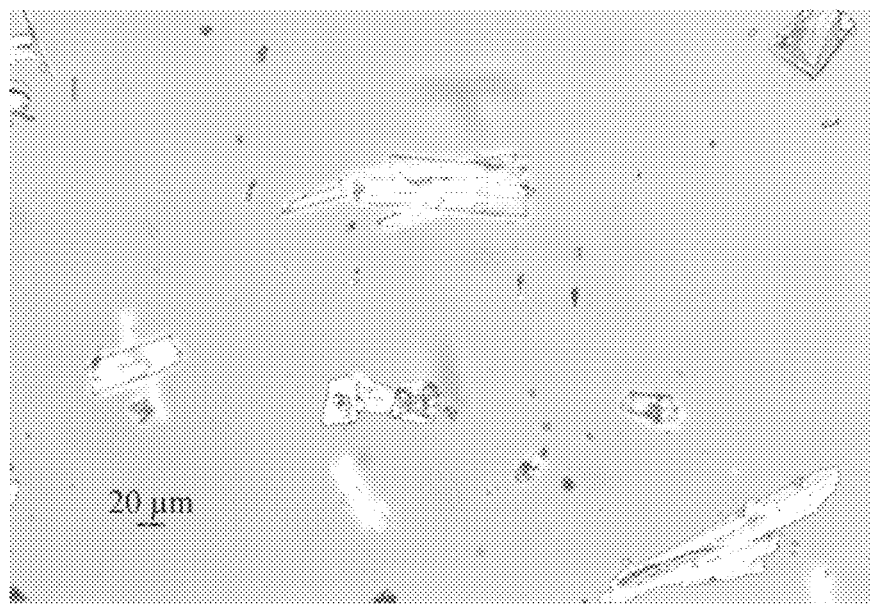
FIG. 45 shows a PLM image of Form CS3 in Example 28.
Figure 46:
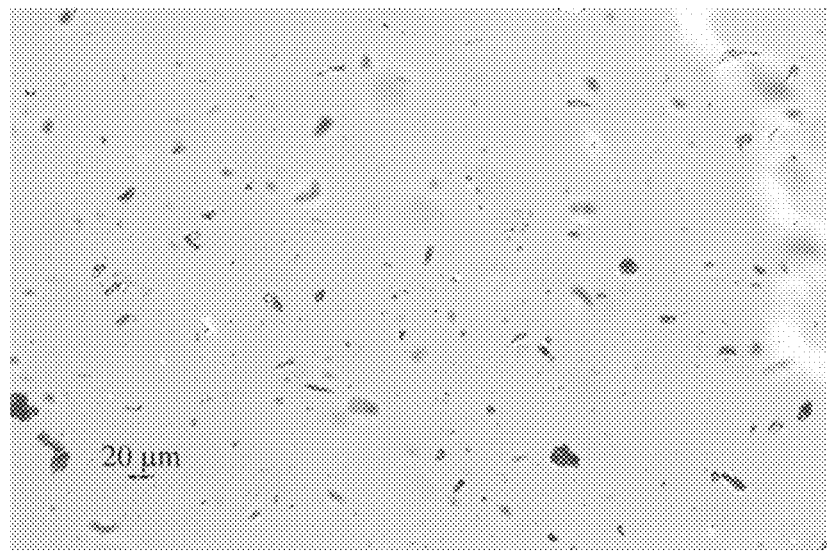
FIG. 46 shows a PLM image of Form CS5 in Example 28.
Figure 47:
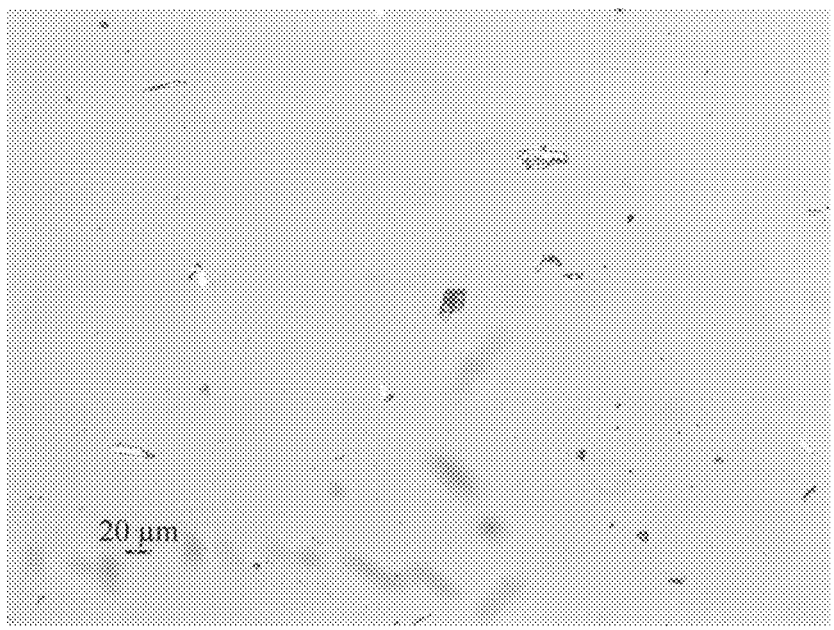
FIG. 47 shows a PLM image of Form CS6 in Example 28.
Figure 48:
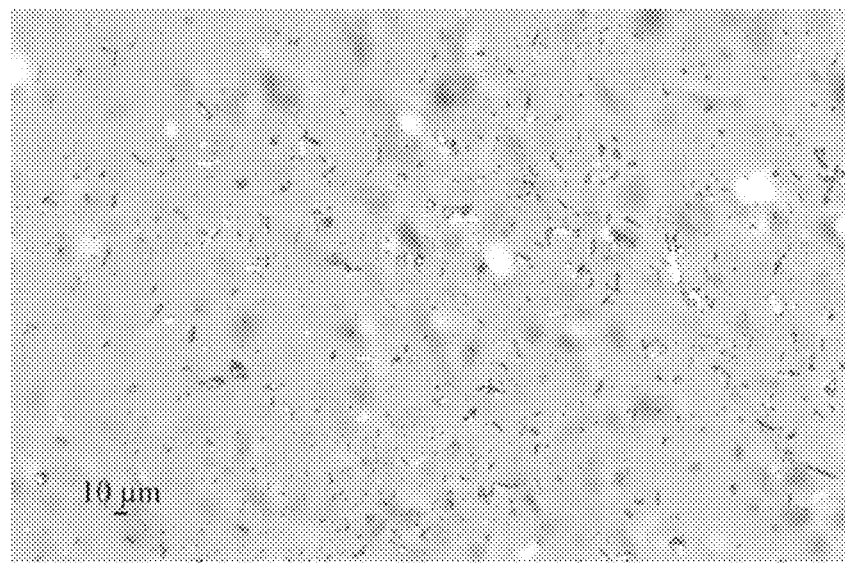
FIG. 48 shows a PLM image of Form CS1 of hydrochloride in Example 28.
Figure 49:
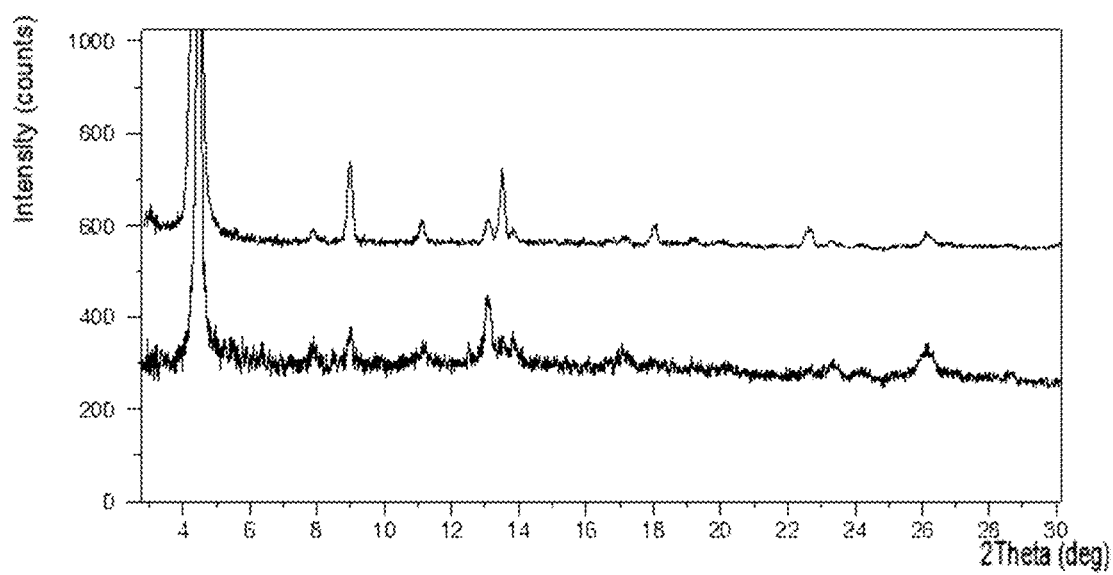
FIG. 49 shows an XRPD comparison pattern of Form CS3 before and after grinding test in Example 31.
Figure 50:
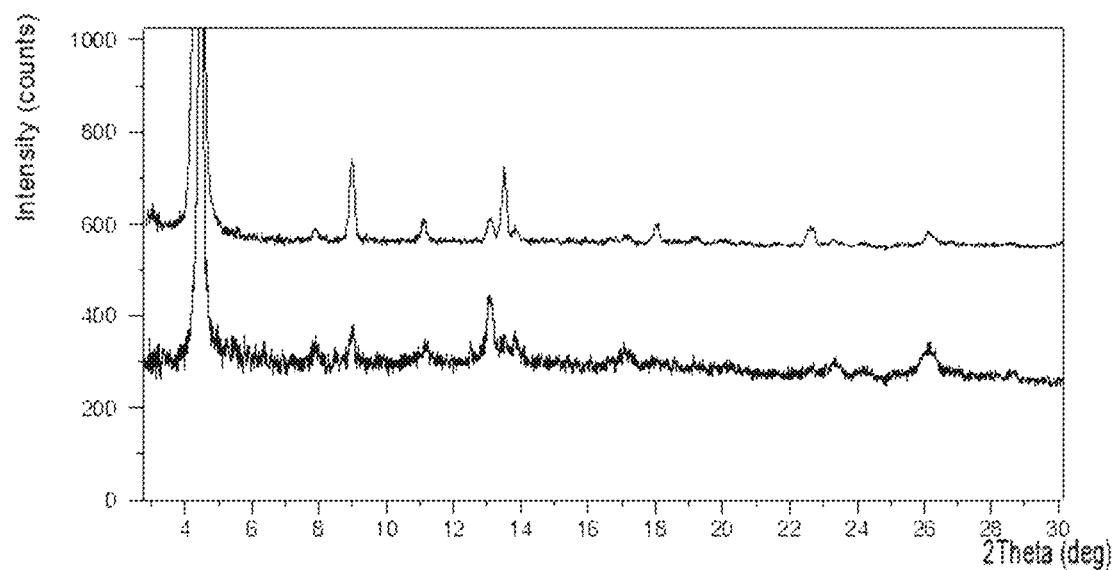
FIG. 50 shows an XRPD comparison pattern of Form CS5 before and after grinding test in Example 31.
Figure 51:
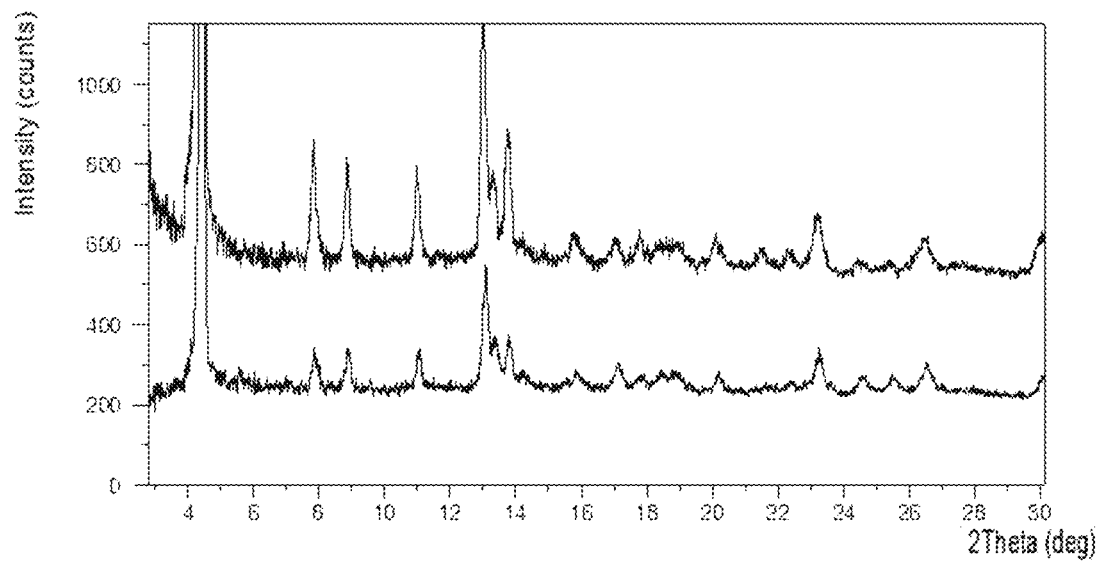
FIG. 51 shows an XRPD comparison pattern of Form CS6 before and after grinding test in Example 31.
Figure 52:
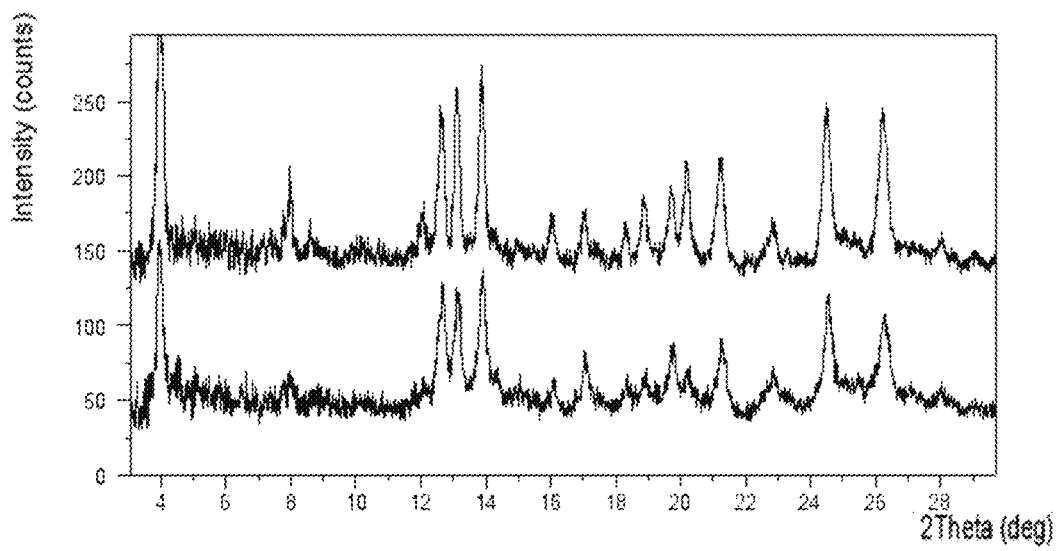
FIG. 52 shows an XRPD comparison pattern of Form CS1 of hydrochloride before and after grinding test in Example 31.

The particle size distribution diagram of Form CS1 of ozanimod hydrochloride is shown in FIG. 42. The result shows that the average particle size of Form CS1 of ozanimod hydrochloride is 200.7 μm, and the particle size is large which conducive to separation during production.

Furthermore, PLM plots of Form CS1, Form CS2, Form CS3, Form CS5, Form CS6 of ozanimod and Form CS1 of ozanimod hydrochloride were displayed in FIG. 43, FIG. 44, FIG. 45, FIG. 46, FIG. 47 and FIG. 48 respectively. Form CS3 was flake-like, Form CS1, Form CS2, Form CS5, Form CS6 and Form CS1 of ozanimod hydrochloride were short rod-like with good dispersion, less agglomeration and uniform particle size.

Uniform particle size helps to simplify the post-treatment process and improve quality control.

Example 29

Solubility Assessment of Form CS1 of Ozanimod and Form CS1 of Ozanimod Hydrochloride:

Form CS1 and Form CS1 of ozanimod hydrochloride were suspended into SGF (Simulated gastric fluids) and FeSSIF (Fed state simulated intestinal fluids, pH=5.0) to obtain saturated solutions. After being equilibrated for 1 h, 4 h and 24 h, concentrations of the saturated solutions were measured by HPLC. The results were listed in Table 27.

TABLE 27

| | Solubility (mg/mL) | | | |
|---|---|---|---|---|
| | SGF | | FeSSIF | |
| Time (h) | Form CS1 | Form CS1 of ozanimod hydrochloride | Form CS1 | Form CS1 of ozanimod hydrochloride |
| 1 | 6.4 | 0.2 | 4.2 | 1.3 |
| 4 | 6.3 | 0.2 | 7.3 | 1.5 |
| 24 | 5.9 | 0.2 | 7.7 | 1.4 |

Example 30

Solubility Assessment:

Form CS3 and Form CS5 were suspended into SGF (Simulated gastric fluids) and water, and Form CS2 was suspended into FeSSIF (Fed state simulated intestinal fluids) to obtain saturated solutions. After being equilibrated for 1 h, 4 h and 24 h, concentrations of the saturated solutions were measured by HPLC. The results were listed in Table 28.

TABLE 28

| | Solubility (mg/mL) | | | | |
|---|---|---|---|---|---|
| | FeSSIF | SGF | | $H_2O$ | |
| Time (h) | Form CS2 | Form CS3 | Form CS5 | Form CS3 | Form CS5 |
| 1 | 2.0 | 0.54 | 1.4 | 0.17 | 0.24 |
| 4 | 2.2 | 0.52 | 1.0 | 0.24 | 0.26 |
| 24 | 1.1 | 0.54 | 0.77 | 0.35 | 0.27 |

Example 31

Mechanical Stability of Form CS3, Form CS5, Form CS6 of Ozanimod and Form CS1 of Ozanimod Hydrochloride:

Solid samples of Form CS3, Form CS5, Form CS6 of ozanimod and Form CS1 of ozanimod hydrochloride were ground manually for 5 minutes in mortar. The XRPD patterns were displayed in FIG. 49, FIG. 50, FIG. 51 and FIG. 52, respectively (the top pattern is before grinding and bottom pattern is after grinding).

No form change was observed for Form CS3, Form CS5, Form CS6 of ozanimod and Form CS1 of ozanimod hydrochloride under a certain mechanical stress with slightly decrease in crystallinity. Good physical and chemical properties including stability made these forms suitable for drug preparation and storage.

Crystalline forms with better mechanical stability have good physicochemical properties and remain stable under certain mechanical stress. The crystalline drug with better mechanical stability has low requirements on the crystallization equipment, and no special post-treatment condition is required. It is more stable in the formulation process, can significantly reduce the development cost of the drug products, enhance the quality of the drug, and has strong economic value.

It is to be noted that Form CS1 used in Examples 16 to 31 of the present disclosure is prepared by the method of Example 1; Form CS2 is prepared by the method of Example 3; Form CS3 was prepared by the method of Example 6; Form CS5 was prepared by the method of Example 9; Form CS6 was prepared by the method of Example 10; Form CS1 of ozanimod hydrochloride was prepared by the method of Example 11.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure

The invention claimed is:

1. A crystalline Form CS1 of ozanimod hydrochloride, wherein the X-ray powder diffraction pattern shows characteristic peaks at 2theta values of 26.1°±0.20°, 24.4°±0.20° and 20.1°±0.20° using CuKα radiation.

2. The crystalline Form CS1 of ozanimod hydrochloride according to claim 1, wherein the X-ray powder diffraction pattern shows 1 or 2 or 3 characteristic peaks at 2theta values of 3.9°±0.20°, 21.1°±0.20° and 7.9°±0.20° using CuKα radiation.

3. The crystalline Form CS1 of ozanimod hydrochloride according to claim 1, wherein the X-ray powder diffraction pattern shows 1 or 2 or 3 characteristic peaks at 2theta values of 11.9°±0.20°, 19.6°±0.20° and 13.8°±0.20° using CuKα radiation.

4. A process for preparing crystalline Form CS1 of ozanimod hydrochloride according to claim 1, wherein the process comprises method 1) or method 2) or method 3) or method 4) or method 5), 1) adding ozanimod hydrochloride into an ether and stirring at 4-50° C., filtering and drying to obtain a white solid of Form CS1 of ozanimod hydrochloride; said stirring time is at least 0.5 hour; or
2) dissolving ozanimod hydrochloride into a mixture of an alcohol and an ester, evaporating at room temperature to obtain a white solid of Form CS1 of ozanimod hydrochloride; said evaporating time is at least 0.5 day; or
3) dissolving ozanimod hydrochloride into a solvent selected from an amide or a mixture of solvents thereof, then placing the solution in a system containing an antisolvent of ozanimod hydrochloride for liquid vapor diffusion at room temperature, filtering and drying to obtain a white solid of Form CS1 of ozanimod hydrochloride; said diffusion time is at least 1 day; or
4) dissolving ozanimod hydrochloride into a mixture of an alcohol and water to form a supersaturated solution, ozanimod hydrochloride is fully dissolved at 25-80° C. and then filtering, cooling the filtrate for precipitation, filtering and drying to obtain a white solid of Form CS1 of ozanimod hydrochloride; or
5) dissolving ozanimod hydrochloride into an alcohol in a concentration of 12 mg/mL to form an alcohol solution, filtering and evaporating the alcohol solution at room temperature for 1 week to obtain a white solid of Form CS1 of ozanimod hydrochloride.

5. A pharmaceutical composition, wherein said pharmaceutical composition comprises a therapeutically effective amount of crystalline Form CS1 of ozanimod hydrochloride according to claim 1 and a pharmaceutically acceptable carrier, a diluent or an excipient.

6. A method of treating ulcerative colitis, comprising administering to a patient in need thereof a therapeutically effective amount of crystalline Form CS1 of ozanimod hydrochloride according to claim 1.

7. A method of treating multiple sclerosis, comprising administering to a patient in need thereof a therapeutically effective amount of crystalline Form CS1 of ozanimod hydrochloride according to claim 1.

* * * * *